US010139271B2

(12) United States Patent
Nishiwaki

(10) Patent No.: US 10,139,271 B2
(45) Date of Patent: *Nov. 27, 2018

(54) LIGHT DETECTION DEVICE INCLUDING LIGHT DETECTOR, LIGHT COUPLING LAYER, AND LIGHT SHIELDING FILM, LIGHT DETECTION SYSTEM, AND OPTICAL DEVICE

(71) Applicant: Panasonic Intellectual Property Management Co., Ltd., Osaka (JP)

(72) Inventor: Seiji Nishiwaki, Hyogo (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/171,817

(22) Filed: Jun. 2, 2016

(65) Prior Publication Data

US 2016/0360967 A1    Dec. 15, 2016

(30) Foreign Application Priority Data

Jun. 9, 2015   (JP) .................. 2015-116325

(51) Int. Cl.
  *G01J 1/04*   (2006.01)
  *G02B 6/34*   (2006.01)
  (Continued)

(52) U.S. Cl.
  CPC ........... *G01J 1/0422* (2013.01); *G01J 1/0448* (2013.01); *G02B 6/00* (2013.01); *G02B 6/34* (2013.01);
  (Continued)

(58) Field of Classification Search
  CPC ..... C09K 11/02; C09K 11/565; C09K 11/883; B82Y 30/00; G11B 7/22; G11B 7/124; G01J 1/0422; G01J 1/0448
  See application file for complete search history.

(56) References Cited

U.S. PATENT DOCUMENTS 4,815,843 A     3/1989  Tiefenthaler et al.
6,639,887 B1 * 10/2003  Izawa ................ G11B 7/124
                                                 369/112.07
(Continued)

FOREIGN PATENT DOCUMENTS

JP      53-062546      6/1978
JP      62-503053      12/1987
(Continued)

OTHER PUBLICATIONS

Max Born et al., "Principles of Optics", Tokai University Press, pp. 478-485, Dec. 20, 1980.
Goro Nishimura, "Prospects for Near-Infrared Spectroscopy—Possibilities of 1-μm Wavelength Region", The 14th Annual Meeting of Japanese Society for Medical Near Infrared Spectroscopy, vol. 49, 2009, pp. 139-145.

*Primary Examiner* — Michael D Abreu
(74) *Attorney, Agent, or Firm* — McDermott Will & Emery LLP

(57) ABSTRACT

A light detection device according to one aspect of the present disclosure includes: a light detector having a main surface and including at least one first detector and at least one second detector disposed along the main surface; a light coupling layer disposed on or apart from the light detector and including a first low-refractive-index layer, a first high-refractive-index layer disposed on the first low-refractive-index layer and including a first grating, and a second low-refractive-index layer disposed on the first high-refractive-index layer, the first high-refractive-index layer having a higher refractive index than the first and second low-refractive-index layers; and a light shielding film disposed on the light coupling layer and including at least one light transmitting region and at least one light shielding region adjacent to the at least one light transmitting region.

23 Claims, 28 Drawing Sheets

(51) Int. Cl.
 G02B 6/00 (2006.01)
 *A61B 5/00* (2006.01)
(52) U.S. Cl.
 CPC ........... *A61B 5/0042* (2013.01); *A61B 5/0066* (2013.01); *A61B 2562/0233* (2013.01); *A61B 2562/046* (2013.01)

(56) References Cited

U.S. PATENT DOCUMENTS

| | | | |
|---|---|---|---|
| 2001/0015810 A1* | 8/2001 | Hara | G01J 3/26 |
| | | | 359/579 |
| 2003/0174630 A1 | 9/2003 | Izawa | |
| 2007/0034833 A1* | 2/2007 | Parce | B82Y 20/00 |
| | | | 252/301.36 |
| 2011/0236266 A1 | 9/2011 | Uematsu et al. | |
| 2014/0239183 A1 | 8/2014 | Yamazaki et al. | |

FOREIGN PATENT DOCUMENTS

| | | |
|---|---|---|
| JP | 4-089636 | 3/1992 |
| JP | 2000-215504 | 8/2000 |
| JP | 2000-249819 | 9/2000 |
| JP | 2003-233925 | 8/2003 |
| JP | 2011-112564 A | 6/2011 |
| JP | 2011-202997 A | 10/2011 |
| JP | 2014-194410 | 10/2014 |

* cited by examiner

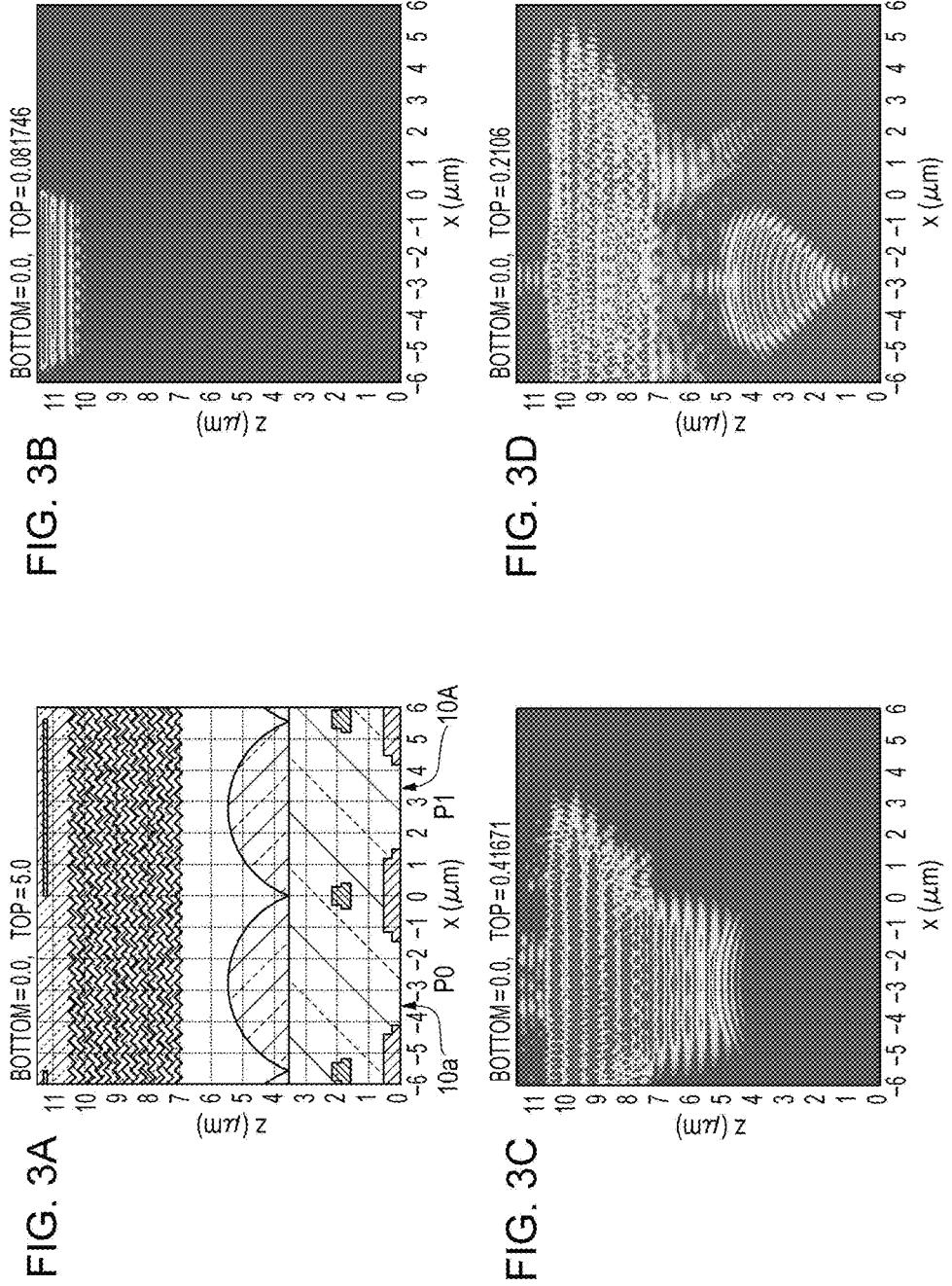

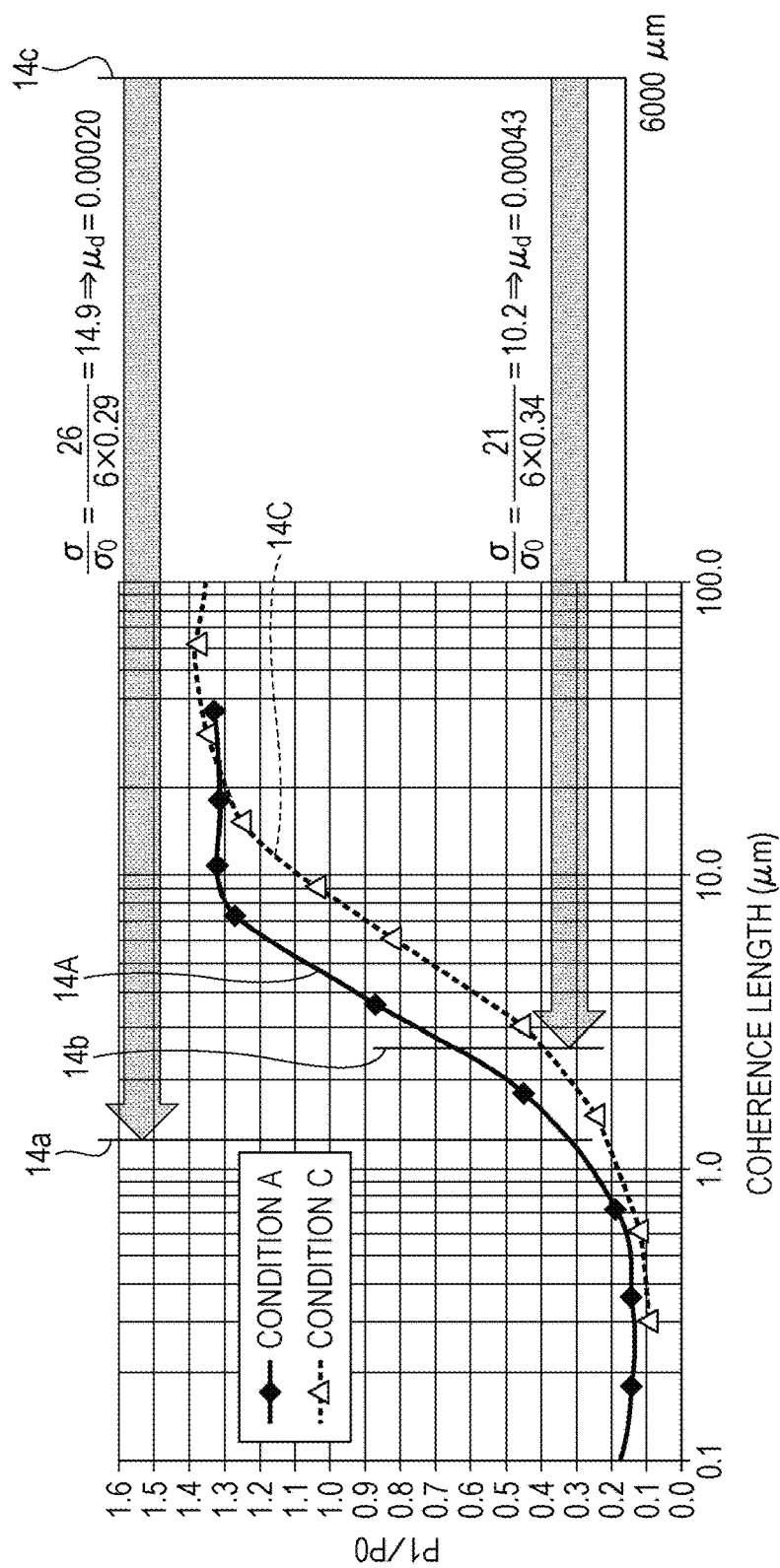

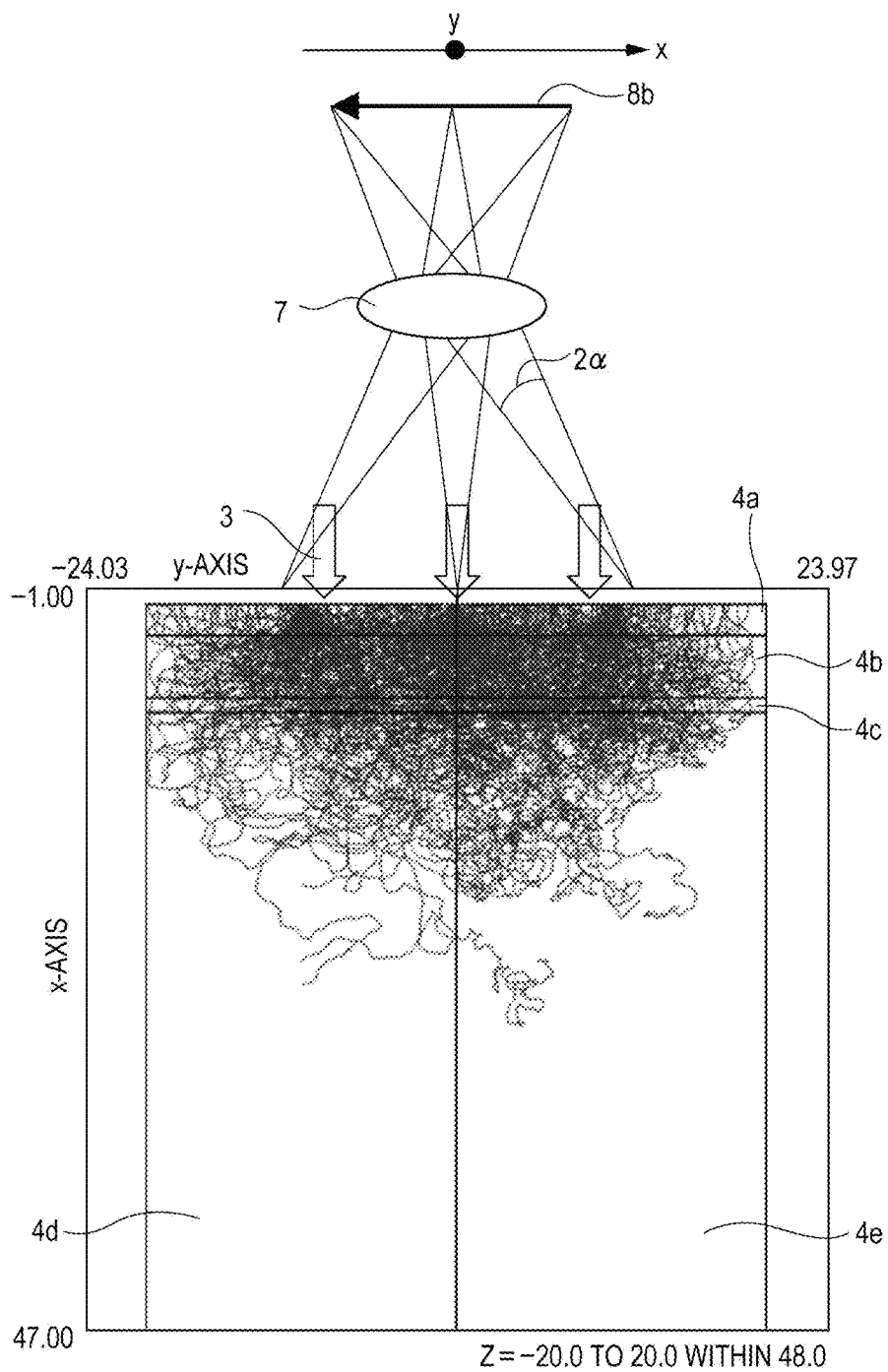

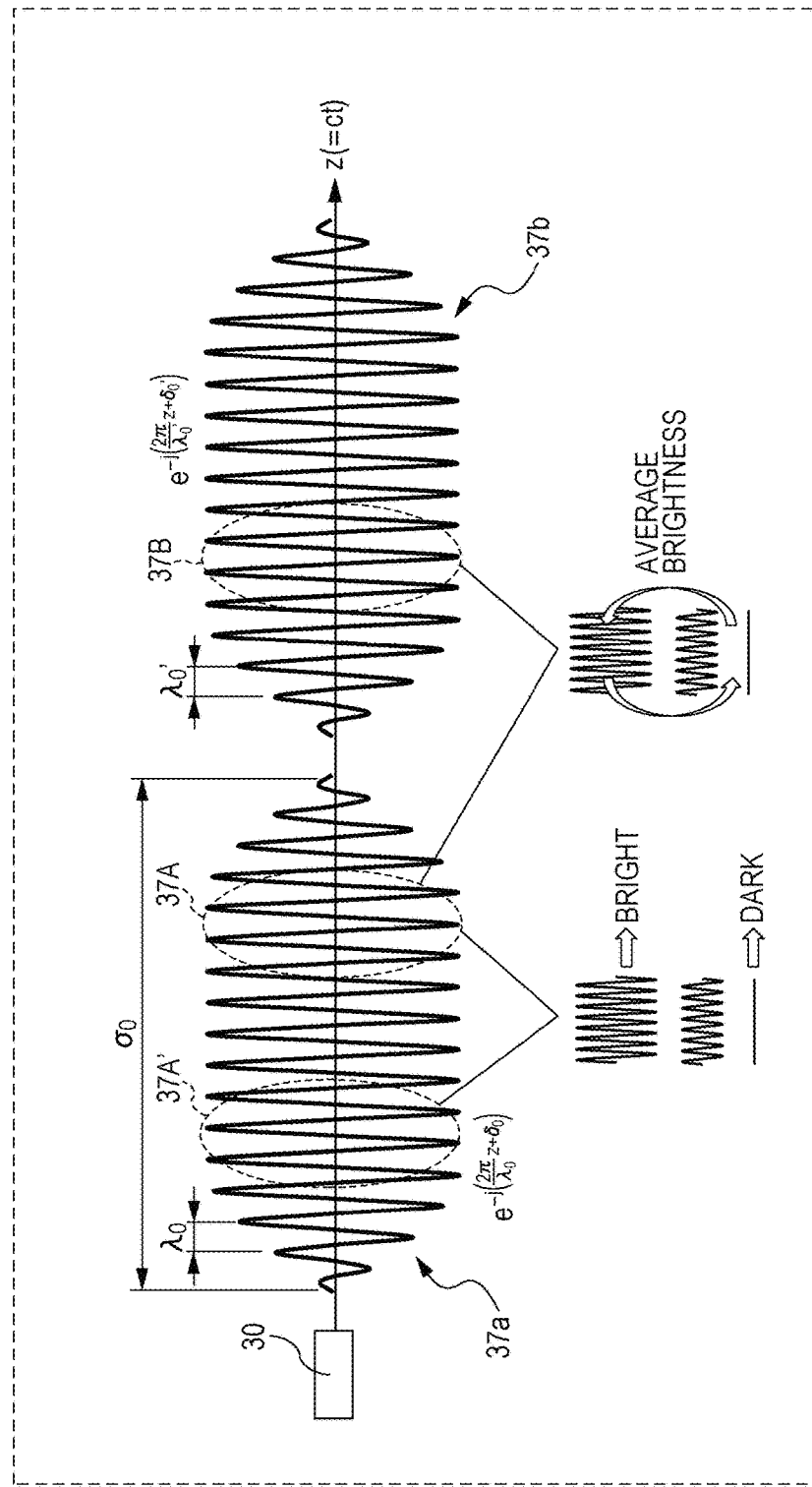

LIGHT DETECTION DEVICE INCLUDING LIGHT DETECTOR, LIGHT COUPLING LAYER, AND LIGHT SHIELDING FILM, LIGHT DETECTION SYSTEM, AND OPTICAL DEVICE

BACKGROUND

1. Technical Field

The present disclosure relates to a light detection device, a light detection system, a light detection method, an optical device, and the like.

2. Description of the Related Art

Light is an electromagnetic wave and is characterized not only by a wavelength and intensity, but also by properties such as polarization or coherence. An example of a method for measuring coherence of light is one using a Michelson interferometer, for example, mentioned in "Principles of Optics" (TOKAI UNIVERSITY PRESS, p. 482, M. Born, et al.).

SUMMARY

In one general aspect, the techniques disclosed here feature a light detection device including: a light detector that has a main surface and includes at least one first detector and at least one second detector that are disposed along the main surface; a light coupling layer disposed on or apart from the light detector, the light coupling layer including a first low-refractive-index layer, a first high-refractive-index layer that is disposed on the first low-refractive-index layer and includes a first grating, and a second low-refractive-index layer that is disposed on the first high-refractive-index layer, the first high-refractive-index layer having a higher refractive index than the first low-refractive-index layer and the second low-refractive-index layer; and a light shielding film disposed on the light coupling layer, the light shielding film including at least one light transmitting region and at least one light shielding region adjacent to the at least one light transmitting region, the at least one light transmitting region corresponding to the at least one first detector, and the at least one light shielding region corresponding to the at least one second detector.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 3A is a cross-sectional view of the light detection device according to First Embodiment;

FIG. 3B is a diagram illustrating, in chronological order, electromagnetic analysis of how 1-pulse incident light passes through a light coupling layer and is then received by detectors in First Embodiment;

FIG. 3C is a diagram illustrating, in chronological order, electromagnetic analysis of how 1-pulse incident light passes through a light coupling layer and is then received by the detectors in First Embodiment;

FIG. 3D is a diagram illustrating, in chronological order, electromagnetic analysis of how 1-pulse incident light passes through a light coupling layer and is then received by the detectors in First Embodiment;

FIG. 4A is an explanatory view illustrating a relationship between a ratio P1/P0 of amounts of light detected by detectors and an effective coherence length (pulse width) of incident light on a certain pulse condition in First Embodiment;

FIG. 10A is a diagram illustrating the entire optical arrangement and light beam tracing in a result calculated by a light beam tracing technique using a Monte Carlo method on the assumption that a subject is a human head;

FIG. 14 is a concept diagram illustrating light emitted from a light source and propagating in a z direction at a time t0 in order to explain a light interference phenomenon;

DETAILED DESCRIPTION

Before description of embodiments of the present disclosure, a result of detailed study of a conventional method for measuring coherence of light is described below.

Figure 13A:
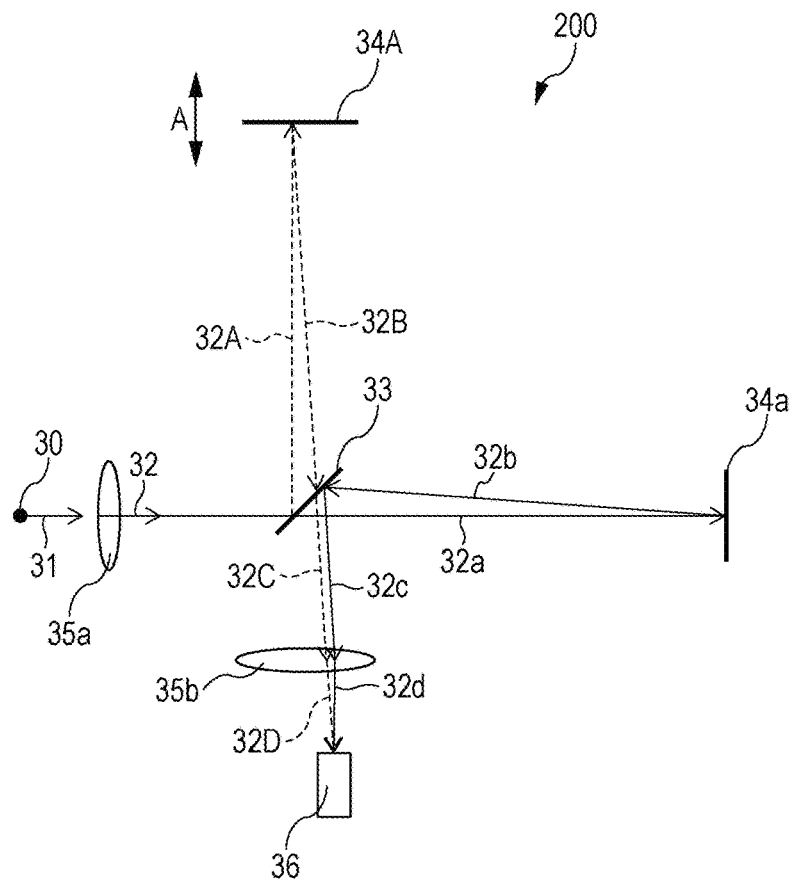
FIG. 13A is an explanatory view illustrating a Michelson interferometer that is a first conventional example and a coherence evaluation method using the Michelson interferometer.

FIG. 13A is an explanatory view illustrating a Michelson interferometer 200, which is a first conventional example, and a method for evaluating coherence by using the Michelson interferometer 200. As illustrated in FIG. 13A, light 31 emitted from a light source 30 is collected by a first light collecting lens 35a, and thus the light 31 becomes parallel light 32. Part of the parallel light 32 passes through a half mirror 33 and travels toward a first reflection mirror 34a (light 32a), is reflected by the first reflection mirror 34a and travels toward the half mirror 33 (light 32b), is reflected by the half mirror 33 and travels toward a second light collecting lens 35b (light 32c), and then enters a detector 36 located on a focal plane of the second light collecting lens 35b (light 32d). Meanwhile, part of the parallel light 32 is reflected by the half mirror 33 and travels toward a second reflection mirror 34A (light 32A), is reflected by the second reflection mirror 34A and travels toward the half mirror 33 (light 32B), passes through the half mirror 33 and travels toward the second light collecting lens 35b (light 32C), and then enters the detector 36 so as to overlap the light 32d (light 32D). The detector 36 detects light obtained by interference between the light 32d and the light 32D. The second reflection mirror 34A is configured such that the position thereof in a direction (arrow A) of an optical axis of a reflection surface is adjustable. A phase of the light 32D relative to the light 32d changes in accordance with a change of the position of the second reflection mirror 34A.

Figure 13B:
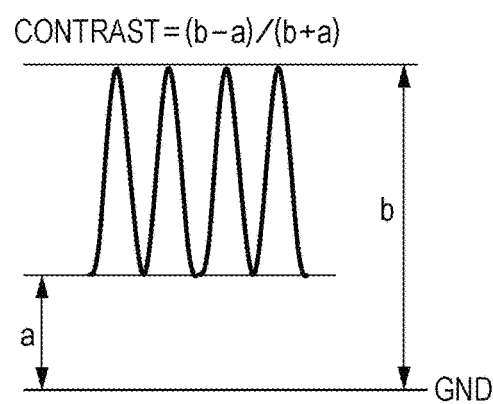
FIG. 13B is a diagram illustrating an electrical signal detected by a detector in the first conventional example.

FIG. 13B illustrates an electrical signal detected by the detector 36. In FIG. 13B, the vertical axis represents the intensity of the signal detected by the detector 36, and the horizontal axis represents time. As illustrated in FIG. 13B, the signal intensity changes in a range from a to b in accordance with passage of time (a change of the position of the second reflection mirror 34A). A value of (b−a)/(b+a) is called contrast in interference, and the degree of coherence of the light 31 is defined by this value. The value of contract changes in accordance with a change of the position of the second reflection mirror 34A in the optical axis direction.

FIG. 14 is a concept diagram illustrating light at a time t0 that is emitted from the light source 30 and propagates in a z direction in order to explain a light interference phenomenon. As illustrated in FIG. 14, wave trains 37a, 37b, and the like are sequentially emitted from the light source 30. The length $\sigma_0$ of a wave train is called coherence length. Waves in a wave train are continuous and have a uniform wavelength. There is no correlation in phase between difference wave trains (the phase of the wave train 37a is $\delta_0$, and the phase of the wave train 37b $\delta_0'(\delta_0 \neq \delta_0')$), and wavelengths in different wave trains are sometimes different from each other (the wavelength of the wave train 37a is $\lambda_0$, and the wavelength of the wave train 37b is $\lambda_0'$ ($\lambda_0 \neq \lambda_0'$)). For example, in the optical system illustrated in FIG. 13A, interference is caused between a part 37A and a part 37A' of the wave train 37a by adjusting a change of the position of the second reflection mirror 34A. The waves in the part 37A and the waves in the part 37A' have equal wavelengths, and a phase difference between the part 37A and the part 37A' is stable over time (kept at a certain value). Accordingly, brightness of light after interference (the amplitude of interference light) is stable over time (kept at certain brightness). That is, the interference light looks bright or looks dark in accordance with the amount of phase difference (a change of the position of the reflection mirror 34A) (this state is called a coherent state). Meanwhile, a case where interference is caused between the part 37A of the wave train 37a and a part 37B of the wave train 37b is discussed below. In this case, there is no guarantee that the waves in the part 37A and the waves in the part 37B have equal wavelengths, and a phase difference between the waves in the part 37A and the waves in the part 37B randomly changes over time. Accordingly, brightness of light after interference (the amplitude of interference light) also randomly changes over time. This change occurs at a femtosecond rate. Accordingly, the interference light alternates between bright and dark states at a high rate, and appear to human eyes as average brightness (this state is called an incoherent state). Laser light, which has a long wave train and has a coherence length of approximately several m to several hundred m, is a representative of coherent light. Meanwhile, solar light, which has a short wave train and has a coherence length of approximately 1 μm, is a representative of incoherent light. In a case where interference of light, such as laser light, that has a long coherence length is caused in the configuration illustrated in FIG. 13A, the probability of interference within the same wave train is high and the contrast improves (close to 1). Meanwhile, in the case of light, such as solar light, that has a short coherence length, the probability of interference between different wave trains is high and the contrast decreases (close to 0).

Figure 15A:
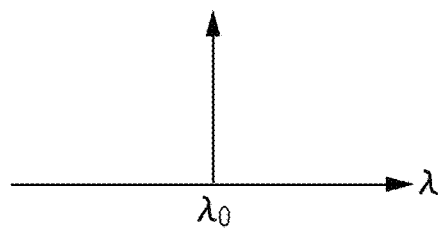
FIG. 15A is an explanatory view illustrating a relationship between expanse of a wavelength of light (longitudinal mode width) and a coherence length.
Figure 15B:
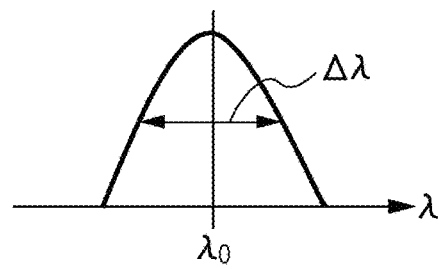
FIG. 15B is an explanatory view illustrating a relationship between expanse of a wavelength of light (longitudinal mode width) and a coherence length.
Figure 15C:
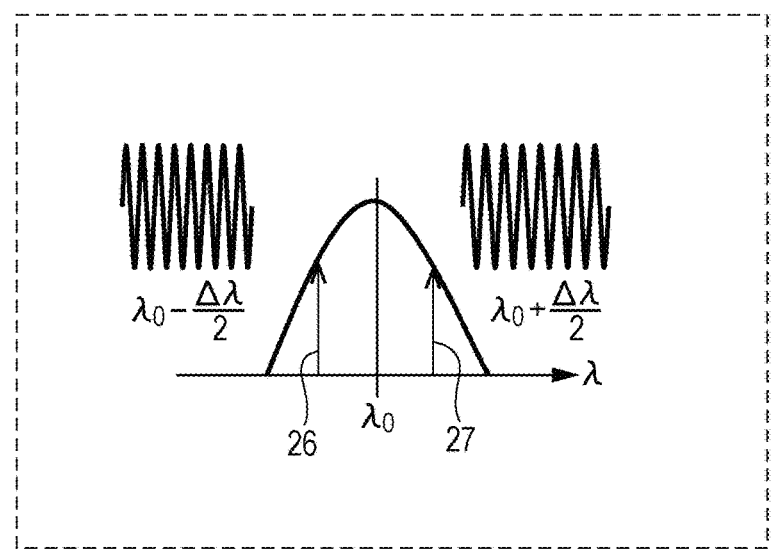
FIG. 15C is an explanatory view illustrating a relationship between expanse of a wavelength of light (longitudinal mode width) and a coherence length.
Figure 15D:
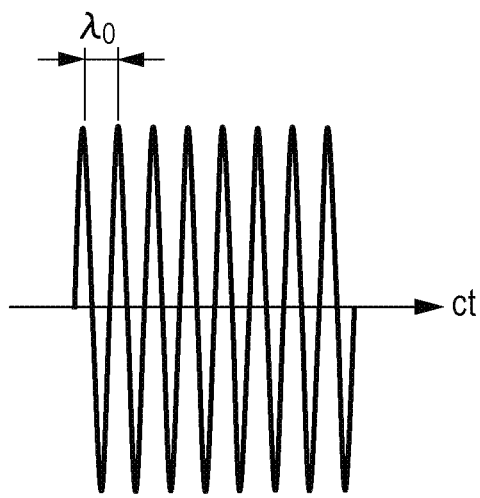
FIG. 15D is an explanatory view illustrating a relationship between expanse of a wavelength of light (longitudinal mode width) and a coherence length.
Figure 15E:
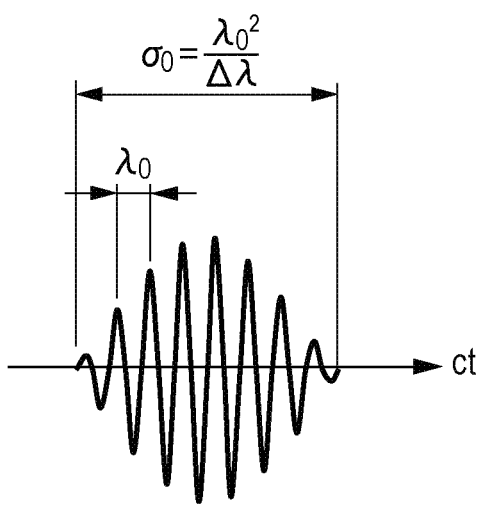
FIG. 15E is an explanatory view illustrating a relationship between expanse of a wavelength of light (longitudinal mode width) and a coherence length.

FIGS. 15A through 15E illustrate a relationship between expanse of wavelength (longitudinal mode width) of light from the wavelength $\lambda_0$ and a coherence length of the light. FIG. 15A illustrates a case where the expanse of wavelength from the wavelength $\lambda_0$ is zero. In this case, the coherence length is infinite as illustrated in FIG. 15D. FIG. 15B illustrates a case where the expanse of wavelength from the wavelength $\lambda_0$ is $\Delta\lambda$. In this case, the coherence length $\sigma_0$ is $\lambda_0^2/\Delta\lambda$ as illustrated in FIG. 15E. The longitudinal mode width and the coherence length are in a relationship of Fourier transform and is called a Wiener-Khinchin theorem. This can be explained as follows. In FIG. 15C, the light whose expanse of wavelength from the wavelength $\lambda_0$ is $\Delta\lambda$ is replaced with light 26 having a wavelength of $\lambda_0-\Delta\lambda/2$ and light 27 having a wavelength of $\lambda_0+\Delta\lambda/2$. A cycle of a beat that occurs due to interference between the light 26 and the light 27 is $\lambda_0^2/\Delta\lambda$, and a wavelength of a carrier wave is an average $\lambda_0$ of the wavelength of the light 26 and the wavelength of the light 27. Within the cycle of the beat, an oscillatory waveform of light is uniform and continuous. Meanwhile, between different cycles, continuity of an oscillatory waveform of light is lost, and correlation in phase is also lost. That is, the cycle of the beat $\lambda_0^2/\Delta\lambda$ is a coherence length. The reason why solar light is incoherent is that expanse of wavelength (longitudinal mode width) $\Delta\lambda$ is large, and the coherence length $\sigma_0$ is $\lambda_0^2/\Delta\lambda=1.0$ in a case where the central wavelength $\lambda_0$ is set to 0.55 μm and the expanse $\Delta\lambda$ of wavelength is set to 0.30 μm.

Figure 16A:
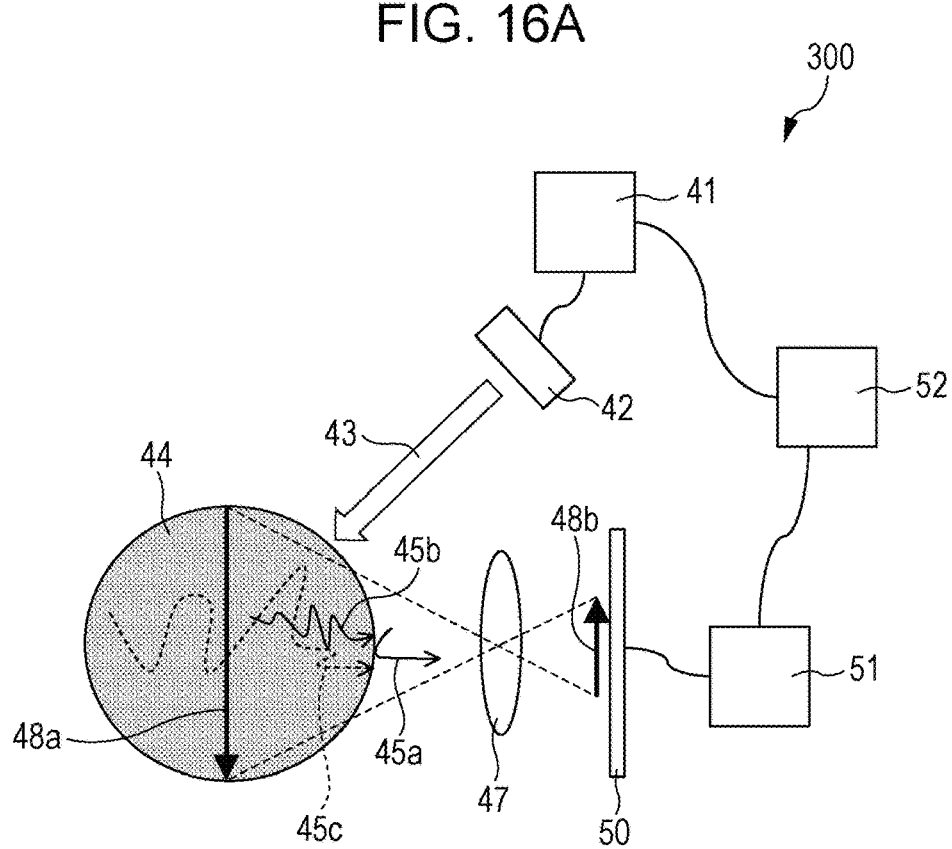
FIG. 16A is a cross-sectional view schematically illustrating a light detection system of a second conventional example.

Next, a light detection system mentioned in "Near-infrared Spectroscopy in a 1-μm Wavelength Region: Current and Future" (The 14th Annual Meeting of Japanese Society for Medical Near Infrared Spectroscopy, pp. 139-144, Goro NISHIMURA) is described as a second conventional example. The light detection system mentioned in "Near-infrared Spectroscopy in a 1-μm Wavelength Region: Current and Future" (The 14th Annual Meeting of Japanese Society for Medical Near Infrared Spectroscopy, pp. 139-144, Goro NISHIMURA) measures a light intensity distribution at each distance. FIG. 16A is a schematic cross-sectional view of a light detection system 300 in the second conventional example. A light source 42 emits laser light. As illustrated in FIG. 16A, light 43 having a wavelength $\lambda_0$ is emitted from the light source 42 toward a subject 44. As a result, scattered light 45a, 45b, and 45c generated on a surface of the subject 44 or in the subject 44 is collected by a light collecting lens 47 and forms an image 48b on an image formation plane of the light collecting lens 47 (a substantial object (a collection of object points) 48a corresponding to the image 48b exists on an object side of the lens). A detector 50 is disposed on the image formation plane. The detector 50 is a collection of a plurality of pixels and detect the amount of incident light in each pixel. Light emission of the light source 42 is controlled by a controller 41. The amount of light detected by the detector 50 is processed in an arithmetic circuit 51 as a detection signal. The controller 41 and the arithmetic circuit 51 are collectively controlled by a computer 52.

Figure 16B:
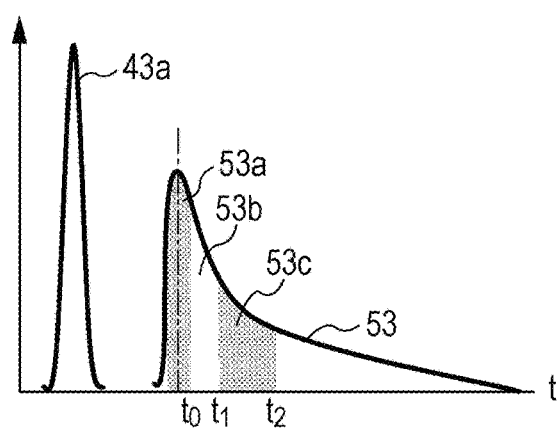
FIG. 16B is an explanatory view illustrating a relationship between oscillation of a light source and a signal detected by a detector in the light detection system of the second conventional example.

FIG. 16B is an explanatory view illustrating a relationship between oscillation of the light source 42 and a signal detected by the detector 50 in the light detection system 300 illustrated in FIG. 16A. The light source 42 oscillates a pulse 43a under control of the controller 41. The light 43 having the pulse 43a is scattered in the subject 44 and is received and detected as a signal 53 by the detector 50. In FIG. 16B, the vertical axis represents an oscillation intensity of the light source 42 or a detection intensity of the detector 50, and the horizontal axis represents an elapsed time. The detected signal 53 is wider in time width than the original pulse 43a due to an influence of a variation in optical path length caused by scattering. An output 53a at the beginning of the detected signal 53 is a signal of light 45a reflected by the surface of the subject 44. An output 53b between a time t0 and a time t1 after the output 53a is a signal of light 45b that is scattered in the subject 44 and whose scattering distance is short. An output 53c between the time t1 and a time t2 after the output 53b is a signal of light 45c whose scattering distance is long. The arithmetic circuit 51 time-divides the detected signal 53 under control of the computer 52 so that the outputs of the signals 53a, 53b, and 53c can be separately detected. Since the depth in the subject which the light passes through becomes deeper in the order of the outputs 53a, 53b, and 53c, pieces of information of different depths can be separated and analyzed.

Figure 17:
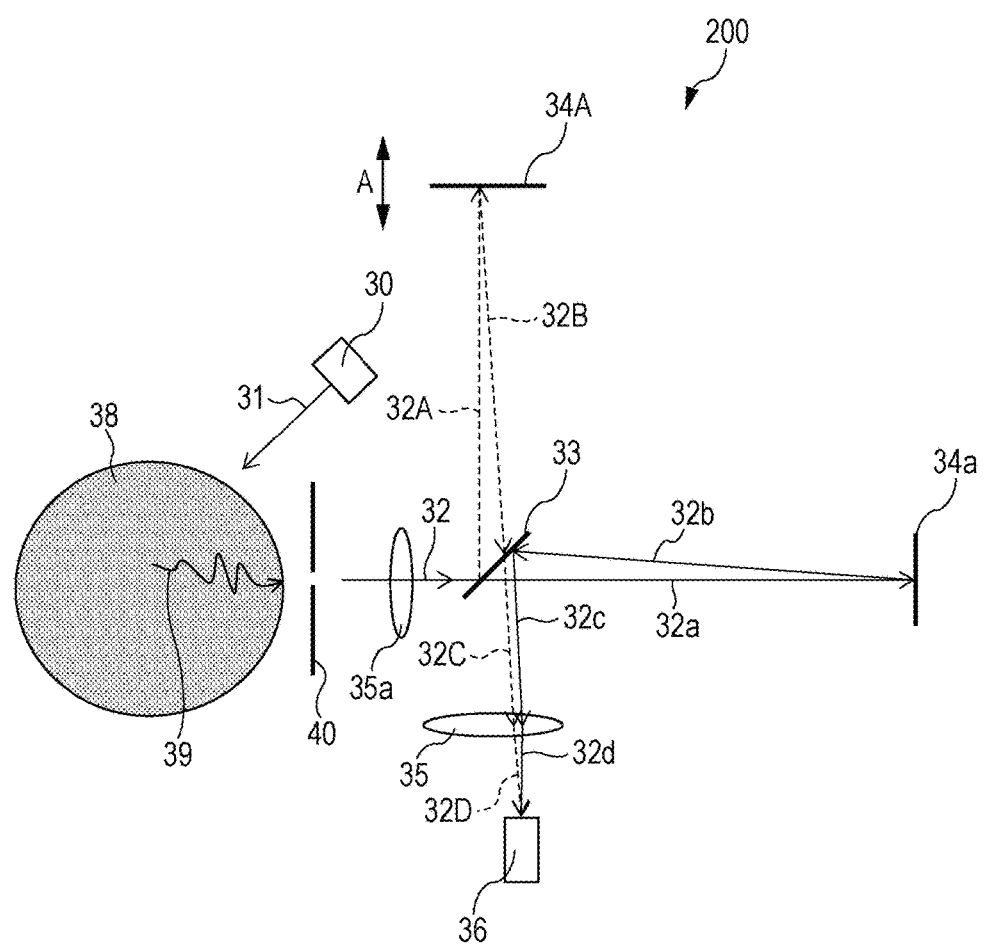
FIG. 17 is a cross-sectional view schematically illustrating an example of application of the first conventional example.

According to the study of the inventor of the present disclosure, the position of measurement of the degree of coherence using the Michelson interferometer 200 that is the first conventional example is limited to the position of the light source 30, i.e., one point within a plane orthogonal to a light propagation direction. For example, assume that the light 31 is emitted from the light source 30 toward a subject 38, and scattered light 39 is collected to cause interference by using the Michelson interferometer 200 illustrated in FIG. 13A, as illustrated in FIG. 17. A propagation direction of the scattered light 39 is spatially expanded. Accordingly, even in a case where the scattered light 39 enters and is collected by the light collecting lens 35a as it is, the light thus collected does not become parallel light. It is therefore impossible to measure the degree of coherence. A pinhole 40 need be provided on the focal plane of the light collecting lens 35a so that the light collected by the light collecting lens 35a becomes parallel light 32. By passing the scattered light 39 through the pinhole 40, the light collected by the light collecting lens 35a can be turned into the parallel light 32. However, in this configuration, the position of measurement of the degree of coherence is limited to the position of the pinhole 40, i.e., one point within a plane orthogonal to a light propagation direction. Furthermore, the scale of the whole interferometer becomes large, and a troublesome operation of moving the reflection mirror 34A is needed to measure the degree of coherence.

Meanwhile, according to the study of the inventor of the present disclosure, the light detection system that is the second conventional example has a limitation on the width of a divided time. It is therefore impossible to sufficiently secure resolution in a depth direction in diagnosis. For example, in a case where the width of a divided time is 300 ps, the depth resolution is approximately 90 mm, and is not suitable for diagnosis and inspection of a relatively small target such as a biological object.

A light detection device according to a first aspect of the present disclosure includes: a light detector that has a main surface and includes at least one first detector and at least one second detector that are disposed along the main surface; a light coupling layer disposed on or apart from the light detector, the light coupling layer including a first low-refractive-index layer, a first high-refractive-index layer that is disposed on the first low-refractive-index layer and includes a first grating, and a second low-refractive-index layer that is disposed on the first high-refractive-index layer, the first high-refractive-index layer having a higher refractive index than the first low-refractive-index layer and the second low-refractive-index layer; and a light shielding film disposed on the light coupling layer, the light shielding film including at least one light transmitting region and at least one light shielding region adjacent to the at least one light transmitting region, the at least one light transmitting region corresponding to the at least one first detector, and the at least one light shielding region corresponding to the at least one second detector. In the light detection device according to the first aspect, the at least one light transmitting region may face the at least one first detector, and the at least one light shielding region may face the at least one second detector. In the light detection device according to the first aspect, the light detector may be a charge-coupled device (CCD). In the light detection device according to the first aspect, the light detector may be an optical imaging system. In operation, the optical imaging system may detect a distribution of a light intensity. The optical imaging system may include a camera or a microscope.

According to this light detection device, part of light that enters the light detection device is blocked by a light shielding region, and the other part of the light passes through a light transmitting region and enters a light coupling layer. The light that enters the light coupling layer is separated into light that passes through the light coupling layer and enters a first detector facing the light transmitting region and light that propagates in a first high-refractive-index layer. Part of the light that propagates in the first high-refractive-index layer is radiated and enters a second detector facing a light shielding region adjacent to the light transmitting region. That is, the light that passes through the light coupling layer can be detected by the first detector facing the light transmitting region. Furthermore, the light that propagates in the first high-refractive-index layer can be detected by the second detector facing the light shielding region. The degree of effective coherence of the light that has entered the light detection device can be measured without a complicated operation by using the amounts of these two kinds of detected light.

In the light detection device according to the first aspect, a light detection device according to a second aspect of the present disclosure is arranged such that the at least one first detector comprises first detectors; the at least one second detector comprises second detectors; the first detectors and the second detectors are two-dimensionally disposed along the main surface; the at least one light transmitting region comprises light transmitting regions; the at least one light shielding region comprises light shielding regions; each of the light transmitting regions corresponds to at least one of the first detectors; and each of the light shielding regions corresponds to at least one of the second detectors. In the light detection device according to the second aspect, each of the light transmitting regions may face at least one of the first detectors, and each of the light shielding regions may face at least one of the second detectors.

According to this light detection device, the degree of effective coherence of light can be measured as in-plane distribution information.

In the light detection device according to the second aspect, a light detection device according to a third aspect of the present disclosure is arranged such that the light shielding regions are disposed in a striped pattern or a checkered pattern in plan view.

In the light detection device according to the first aspect, a light detection device according to a fourth aspect of the present disclosure is arranged such that the light detector further includes: a first microlens disposed between the at least one first detector and the light coupling layer; and a second microlens disposed between the at least one second detector and the light coupling layer.

In the light detection device according to any one of the first through third aspects, a light detection device according to a fifth aspect of the present disclosure is arranged such that the light coupling layer further includes: a third low-refractive-index layer; and a second high-refractive-index layer that is disposed between the third low-refractive-index layer and the first low-refractive-index layer and includes a second grating; and the second high-refractive-index layer has a higher refractive index than the first low-refractive-index layer and the third low-refractive-index layer.

In the light detection device according to the fifth aspect of the present disclosure, the pitch of the first grating and the pitch of the second grating may be different from each other.

In the light detection device according to the fifth aspect of the present disclosure, the thickness of the first high-refractive-index layer and the thickness of the second high-refractive-index layer may be different from each other.

A light detection system according to a sixth aspect of the present disclosure includes the light detection device according to the first aspect and a light source.

According to this light detection system, part of light that is emitted from a light source, passes through or is reflected by a subject, and then enters a light detection device is blocked by a light shielding region, and the other part of the light passes through a light transmitting region and enters a light coupling layer. The light that enters the light coupling layer is separated into light that passes through the light coupling layer and enters a first detector facing the light transmitting region and light that propagates in a first high-refractive-index layer. Part of the light that propagates in the first high-refractive-index layer is radiated and enters a second detector facing a light shielding region adjacent to the light transmitting region. That is, the light that passes through the light coupling layer can be detected by the first detector facing the light transmitting region. Furthermore, the light that propagates in the first high-refractive-index layer can be detected by the second detector facing the light shielding region. The degree of effective coherence of the light that is emitted from a light source, passes through or is reflected by a subject, and enters the light detection device can be measured without a complicated operation by using the amounts of these two kinds of detected light.

In the light detection system according to the sixth aspect, a light detection system according to a seventh aspect of the present disclosure is arranged to further include an arithmetic circuit that, in operation, calculates a ratio of a first signal detected by the at least one first detector and a second signal detected by the at least one second detector.

According to this light detection system, a ratio of the amounts of the two kinds of detected light is calculated. The degree of effective coherence of light can be measured by using this ratio.

In the light detection system according to the sixth aspect, a light detection system according to an eighth aspect of the present disclosure is arranged to further include an arithmetic circuit that, in operation, calculates at least one selected from a group consisting of proportion of a first signal detected by the at least one first detector and proportion of a second signal detected by the at least one second detector in a sum of the first signal and the second signal.

In the light detection system according to the seventh aspect, a light detection system according to a ninth aspect of the present disclosure is arranged such that the at least one first detector comprises first detectors; the at least one second detector comprises second detectors; the first detectors and the second detectors are two-dimensionally disposed along the main surface; the at least one light transmitting region comprises light transmitting regions; the at least one light shielding region comprises light shielding regions; each of the light transmitting regions corresponds to at least one of the first detectors; each of the light shielding regions corresponds to at least one of the second detectors; and the arithmetic circuit, in operation, calculates the ratio for each of the first detectors and generates an image indicative of a distribution of the ratios in the light detector. In the light detection system according to the ninth aspect, each of the light transmitting regions may face at least one of the first detectors, and each of the light shielding regions may face at least one of the second detectors.

In the light detection system according to the eighth aspect, a light detection system according to a tenth aspect of the present disclosure is arranged such that the at least one first detector comprises first detectors; the at least one second detector comprises second detectors; the first detectors and the second detectors are two-dimensionally disposed along the main surface; the at least one light transmitting region comprises light transmitting regions; the at least one light shielding region comprises light shielding regions; each of the light transmitting regions corresponds to at least one of the first detectors; each of the light shielding regions corresponds to at least one of the second detectors; and the arithmetic circuit, in operation, calculates, for each of the first detectors, at least one selected from the group consisting of the proportion of the first signal and the proportion of the second signal in the sum and generates an image indicative of a distribution of the at least one selected from the group consisting of the proportion of the first signal and the proportion of the second signal in the sum in the light detector. In the light detection system according to the tenth aspect, each of the light transmitting regions may face at least one of the first detectors, and each of the light shielding regions may face at least one of the second detectors.

In the light detection system according to any one of the sixth through tenth aspects, a light detection system according to an eleventh aspect of the present disclosure is arranged such that the light source, in operation, emits pulsed light.

According to this light detection system, the accuracy of measurement of cross-sectional information in a subject can be improved as compared with a case where continuous light is emitted.

In the light detection system according to any one of the sixth through eleventh aspects, a light detection system according to a twelfth aspect of the present disclosure is arranged such that the light detection device further includes a bandpass filter that is disposed on the light coupling layer and, in operation, selectively transmits a wavelength of light emitted by the light source.

According to this light detection system, measurement can be performed while suppressing an influence of disturbance light.

In the light detection system according to any one of the sixth through twelfth aspects, a light detection system according to a thirteenth aspect of the present disclosure is arranged to further include a control circuit that, in operation, changes a coherence length of light emitted from the light source.

According to this light detection system, an effective coherence length can be measured in accordance with a coherence length of light emitted from a light source.

In the light detection system according to the ninth aspect, a light detection system according to a fourteenth aspect of the present disclosure is arranged to further include a control circuit that, in operation, changes a coherence length of light emitted from the light source, and the arithmetic circuit, in operation, generating, for each coherence length changed by the control circuit, the image indicating the distribution of the ratios.

According to this light detection system, an effective coherence length can be measured in accordance with a coherence length of light emitted from a light source. In a case where a coherence length of light emitted from a light source is changed, an effective coherence length of light that has passed through or has been reflected by a subject also changes. There are a region where a rate of change with respect to the effective coherence length is large and a region where a rate of change with respect to the effective coherence length is small. By changing the coherence length of the light emitted from the light source, the ratio can be calculated, for example, in the region where a rate of change with respect to the effective coherence length is large. That is, information of an effective coherence length distribution can be reflected in an image indicative of a distribution of the ratios.

In the light detection system according to the tenth aspect, a light detection system according to a fifteenth aspect of the present disclosure is arranged to further include a control circuit that, in operation, changes a coherence length of light emitted from the light source, and the arithmetic circuit, in operation, generating, for each coherence length changed by the control circuit, the image indicative of the distribution of the at least one selected from the group consisting of the proportion of the first signal and the proportion of the second signal in the sum.

In the light detection system according to the ninth aspect, a light detection system according to a sixteenth aspect of the present disclosure is arranged such that the arithmetic circuit, in operation, calculates, for each of the first detectors, the ratio by using the first signal detected by each of the first detectors within a predetermined time range and the second signal detected by each of the second detectors within the predetermined time range; and the arithmetic circuit, in operation, generates a first image indicative of a distribution of the first signal detected, within the predetermined time range, by a first detector for which the ratio is equal to or larger than a threshold value among the first detectors and a second image indicative of a distribution of the first signal detected, within the predetermined time range, by a first detector for which the ratio is smaller than the threshold value among the first detectors.

According to this light detection system, light extracted by time resolving can be further separated in accordance with the ratio. This makes it possible to, for example, distinguish light scattered in a subject that is extracted by time resolving into forward scattered light and backscattered light.

In the light detection system according to the tenth aspect, a light detection system according to a seventeenth aspect of the present disclosure is arranged such that the arithmetic circuit, in operation, calculates, for each of the first detectors, at least one selected from the group consisting of the proportion of the first signal and the proportion of the second signal in the sum by using the first signal detected by each of the first detectors within a predetermined time range and the second signal detected by each of the second detectors within the predetermined time range; and the arithmetic circuit, in operation, generates a first image indicative of a distribution of the first signal detected, within the predetermined time range, by a first detector for which the proportion of the first signal in the sum is equal to or larger than a threshold value or the proportion of the second signal in the sum is equal to or smaller than the threshold value among the first detectors and a second image indicative of a distribution of the first signal detected, within the predetermined time range, by a first detector for which the proportion of the first signal in the sum is smaller than the threshold value or the proportion of the second signal in the sum is larger than the threshold value among the first detectors.

A light detection method according to an eighteenth aspect of the present disclosure includes separating part of light that is emitted from a light source and passes through or is reflected by a subject into transmitted light that passes through a light coupling layer in which a grating is formed on a waveguide layer and guided light that propagates in the waveguide layer; detecting a first light amount of the transmitted light; and detecting a second light amount of the guided light.

According to this light detection method, transmitted light that passes through a light coupling layer and guided light that propagates in a waveguide layer are separated from each other, and light amounts thereof are detected. The degree of effective coherence of light can be measured without a complicated operation by using the detected light amounts. The effective coherence is defined by the length of waves of a continuous phase.

In the eighteenth aspect, a light detection method according to a nineteenth aspect of the present disclosure includes calculating a ratio of the first light amount and the second light amount.

According to this light detection method, a ratio of the amounts of the two kinds of detected light is calculated. The degree of effective coherence of light can be measured by using this ratio.

In the eighteenth aspect, a light detection method according to a twentieth aspect of the present disclosure includes calculating at least one selected from the group consisting of proportion of the first light amount and the proportion of the second light amount in the sum of the first light amount and the second light amount. An optical device according to a twenty-first aspect of the present disclosure includes: a light coupling layer including a first low-refractive-index layer, a first high-refractive-index layer that is disposed on the first low-refractive-index layer and includes a first grating, and a second low-refractive-index layer that is disposed on the first high-refractive-index layer, the first high-refractive-index layer having a higher refractive index than the first low-refractive-index layer and the second low-refractive-index layer; and a light shielding film disposed on the light coupling layer, the light shielding film including at least one light transmitting region and at least one light shielding region adjacent to the at least one light transmitting region.

Each of the embodiments described below is a general or specific example of the present disclosure. Numerical values, shapes, materials, constituent elements, positions of the constituent elements, and the like described in the embodiments below are examples and do not limit the present disclosure. Among the constituent elements in the embodiments below, constituent elements that are not described in the independent claims that show highest concepts of the present disclosure are described as optional constituent elements.

Embodiments are specifically described below with reference to the drawings.

First Embodiment

Figure 1A:
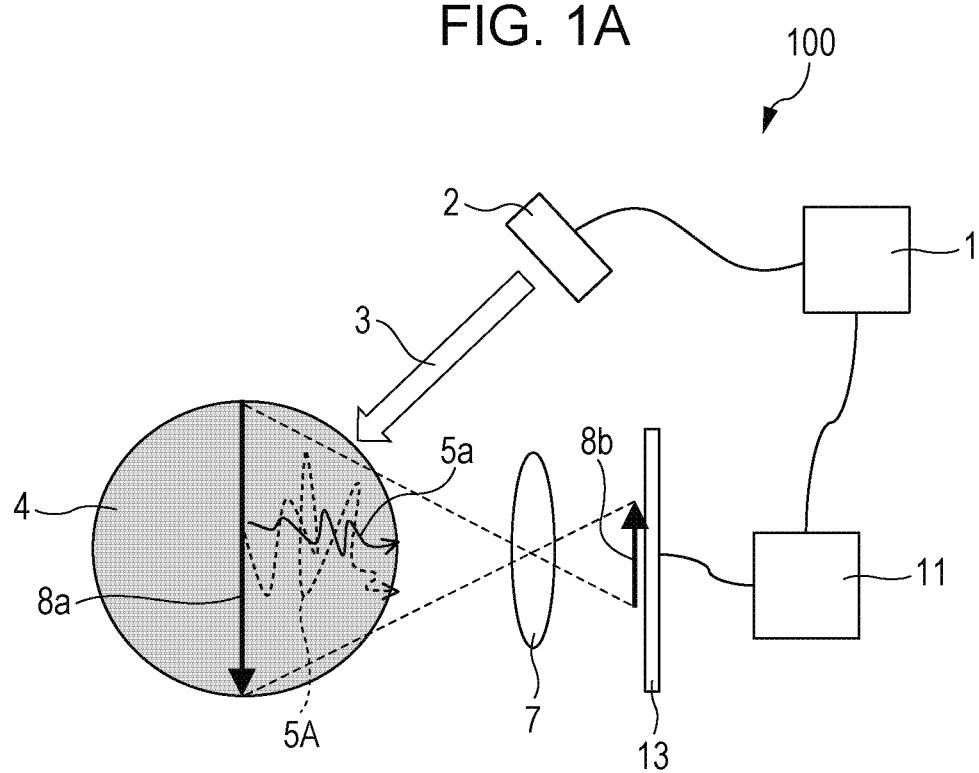
FIG. 1A is a schematic view illustrating a light detection system according to First Embodiment and a subject.

FIG. 1A is a schematic view illustrating a light detection system 100 according to the present embodiment and a subject 4. The light detection system 100 includes a light source 2, a light collecting lens 7, a light detection device 13, a control circuit 1, and an arithmetic circuit 11.

The light source 2 irradiates the subject 4 with light 3 having a constant coherence length. For example, the light 3 emitted from the light source 2 is laser light that is a representative of coherent light. The light source 2 may continuously emit light of a constant intensity or may emit pulsed light. The light 3 emitted from the light source 2 has any wavelength. In a case where the subject 4 is a biological object, the wavelength of the light source 2 can be, for example, set not less than approximately 650 nm and not more than approximately 950 nm. This wavelength range is included in a wavelength range of red to near infrared light. Hereinafter, the term "light" is used not only as visible light, but also as infrared light.

The light collecting lens 7 collects scattered light 5a and 5A that is generated on a surface of the subject 4 or in the subject 4 from the light emitted from the light source 2. The collected light forms an image 8b on an image formation plane of the light collecting lens 7 (a substantial object (a collection of object points) 8a corresponding to the image 8b exists on an object side of the lens). In the example illustrated in FIG. 1A, the light collecting lens 7 includes a single lens, but the light collecting lens 7 may include a plurality of lenses.

The light detection device 13 is disposed on the image formation plane of the light collecting lens 7. The light detection device 13 detects the scattered light 5a and 5A collected by the light collecting lens 7. A detailed structure of the light detection device 13 will be described later.

The arithmetic circuit 11 performs arithmetic processing on a signal detected by the light detection device 13. The arithmetic circuit 11 can be, for example, an image processing circuit such as a digital signal processor (DSP).

The control circuit 1 executes programs recorded, for example, on a memory and controls light detection in the light detection device 13, arithmetic processing in the arithmetic circuit 11, the amount of light emission, an ON timing, a continuous ON period, or a light emission wavelength or a coherence length of the light source 2. The control circuit 1 can be, for example, an integrated circuit such as a central processing unit (CPU) or a microcomputer. The control circuit 1 and the arithmetic circuit 11 may be realized by a unified single circuit.

Note that the light detection system 100 may include a display (not illustrated) on which a result of the arithmetic processing in the arithmetic circuit 11 is displayed.

Figure 1B:
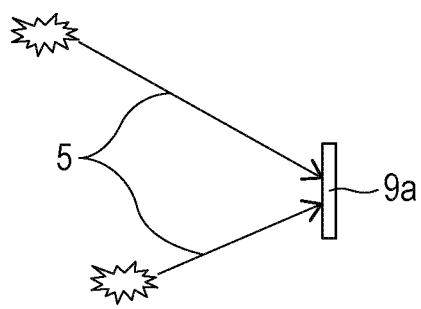
FIG. 1B is an explanatory view illustrating scattered light that enters an opening of a light detector.

FIG. 1B illustrates scattered light 5 that enters a single opening 9a (a "light transmitting region 9a" that will be described later) of the light detection device 13. The subject 4 is a scatterer. A light beam that propagates in the subject 4 repeats attenuation with an attenuation coefficient pa and scattering with a scattering coefficient μs. It is assumed here that n light beams whose coherence length is $\sigma_0$ and whose intensity is 1 are emitted from the light source 2. Furthermore, it is assumed that the amount of light of a k-th light beam emitted from the light source 2 at a timing when the k-th light beam enters the opening 9a while repeating attenuation and scattering is pk. The total amount of light $p_0$ of the light beams that enter the opening 9a is expressed by the formula 1:

$$p_0 = \sum_{k=1}^{n} p_k \qquad \text{formula 1}$$

Figure 2A:
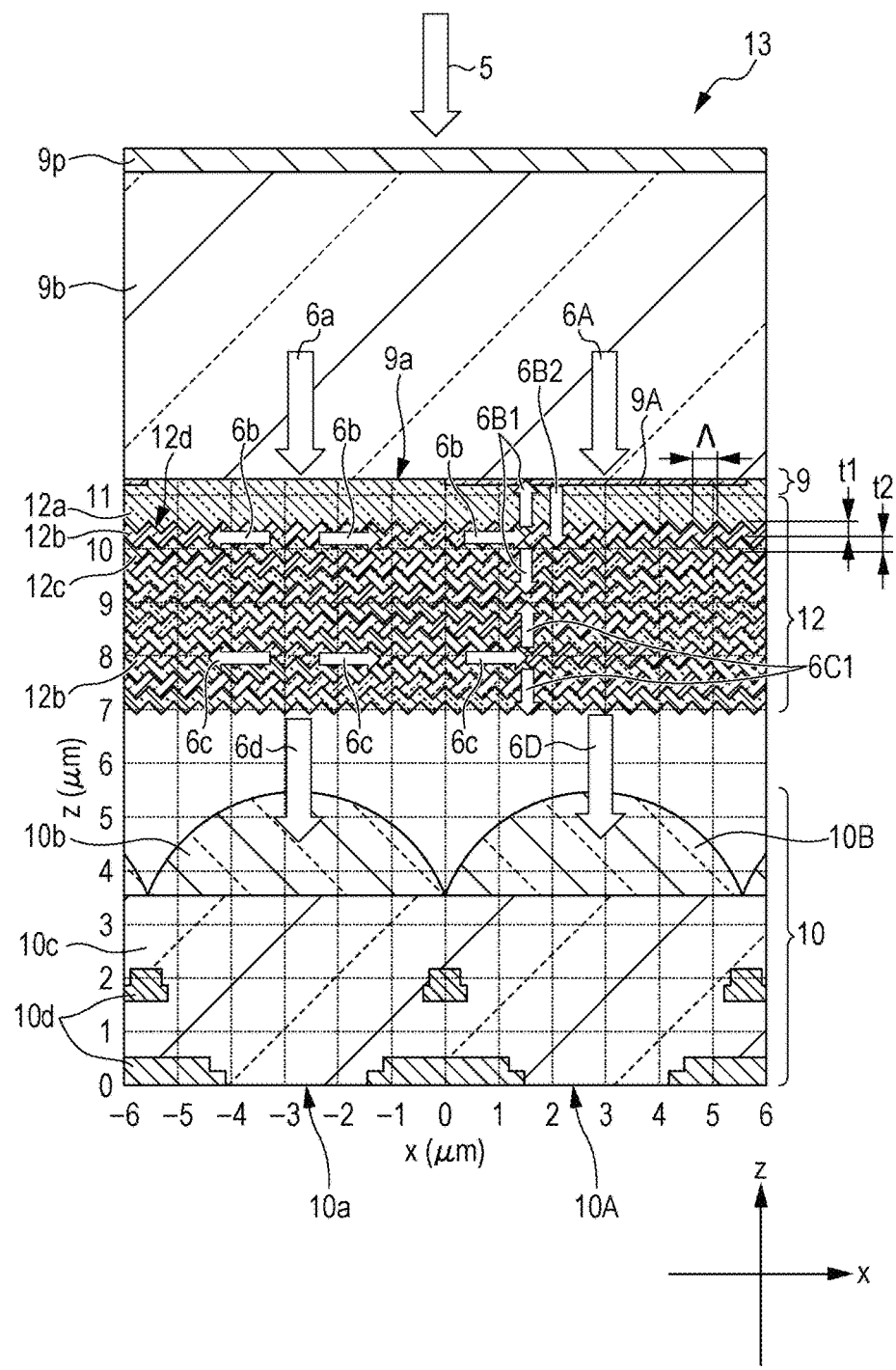
FIG. 2A is a cross-sectional view of a light detection device according to First Embodiment.
Figure 2B:
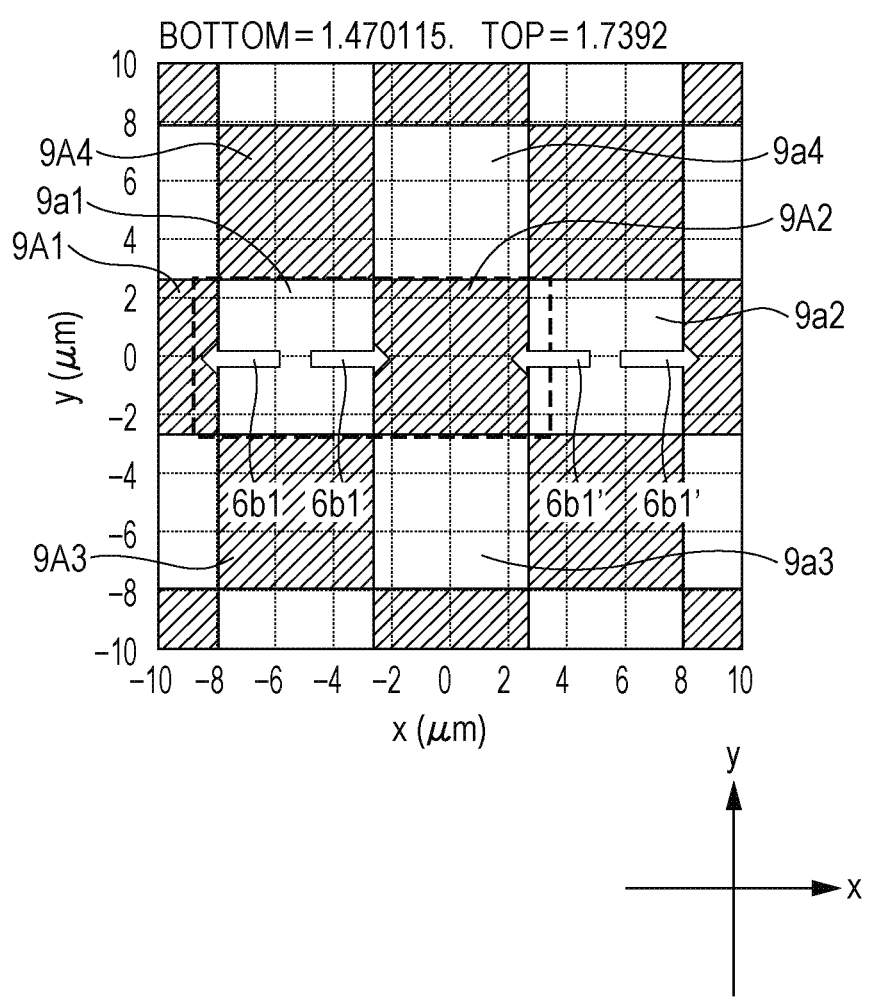
FIG. 2B is a plan view illustrating the light detection device according to First Embodiment viewed from a light incident side.

FIGS. 2A and 2B illustrate a configuration of the light detection device 13. For convenience of description, three axes (an x axis, a y axis, and a z axis) that are orthogonal to each other are illustrated in FIGS. 2A and 2B (these axes are also illustrated in other drawings). FIG. 2B is a plan view of the light detection device 13 viewed from a light incident side, and FIG. 2A is a cross-sectional view of the light detection device 13 taken along a light incident direction (a cross-sectional view taken along the xz plane including a region surrounded by the broken line in FIG. 2B). In FIG. 2B, a cross-sectional structure including a light shielding film (described later) in FIG. 2A that is a cross-sectional view taken along the xz plane is periodically arranged in the xy plane.

The light detection device 13 includes a light detector 10, a light coupling layer 12, and a light shielding film 9 in this order. In the example illustrated in FIG. 2A, these members are stacked in the z direction. Furthermore, in the example illustrated in FIG. 2A, a transparent substrate 9b and a bandpass filter 9p are provided in this order on the light shielding film 9.

The light detector 10 includes a plurality of detectors 10a and 10A disposed in an in-plane direction (within the xy plane) of the light detector 10. The light detector 10 includes microlenses 10b (10B), a transparent film 10c, metal films 10d such as wires, and photosensitive parts made of Si, an organic film, or the like in this order from a light incident side. The photosensitive parts in gaps between the metal films 10d correspond to the detectors 10a and 10A. The plurality of microlenses 10b and 10B are disposed so as to face the respective detectors (10a and 10A), respectively. Light that is collected by the microlenses 10b and 10B and enters the gaps between the metal films 10d is detected by the detectors 10a and 10A.

The light coupling layer 12 is disposed on the light detector 10 and includes a first transparent layer 12c that is a first low-refractive-index layer, a second transparent layer 12b that is a first high-refractive-index layer, and a third transparent layer 12a that is a second low-refractive-index layer in this order in a direction (the z-axis direction) perpendicular to a surface of the light detector 10. The first transparent layer 12c and the third transparent layer 12a are made of $SiO_2$ or the like. The second transparent layer 12b is made of $Ta_2O_5$ or the like. The second transparent layer 12b has a higher refractive index than the first transparent layer 12c and the third transparent layer 12a. The light coupling layer 12 may have a structure in which the highrefractive-index transparent layer 12b and the low-refractive-index transparent layer 12c are alternated in this order. FIG. 2A illustrates a structure in which the high-refractive-index transparent layer 12b and the low-refractive-index transparent layer 12c are alternated six times in total. The high-refractive-index transparent layer 12b is sandwiched between the low-refractive-index transparent layers 12c and 12a and is therefore functions as a waveguide layer. A linear grating 12d of a pitch A is provided all over an interface between the high-refractive-index transparent layer 12b and the low-refractive-index transparent layer 12c and an interface between the high-refractive-index transparent layer 12b and the low-refractive-index transparent layer 12a. A grating vector of the grating 12d is parallel with the x-axis in the in-plane direction (the xy plane) of the light coupling layer 12. An xz cross-sectional shape of the grating 12d is sequentially transferred onto the high-refractive-index transparent layers 12b and the low-refractive-index transparent layers 12c that are stacked (in a case where directivity of film formation of the transparent layers 12b and 12c in the stacking direction is high, transfer of the shape is more easily maintained by making the xz cross section of the grating 12d S-shaped or V-shaped). The grating 12d need just be provided in at least part of the high-refractive-index transparent layer 12b. Since the high-refractive-index transparent layer 12b includes the grating 12d, coupled light propagates in the high-refractive-index transparent layer 12b.

A gap between the light coupling layer 12 and the light detector 10 may be narrow. The light coupling layer 12 and the light detector 10 may be in close contact with each other. This gap (including a space between the microlenses 10b and 10B may be filled with a transparent medium such as an adhesive. In a case where the gap is filled with a transparent medium, the microlenses 10b and 10B can be made of a material having a sufficiently large refractive index than the transparent medium in order to obtain a lens effect in the microlenses 10b and 10B.

The light shielding film 9 has a plurality of light shielding regions 9A and a plurality of light transmitting regions 9a. In the example illustrated in FIG. 2A, the light shielding regions 9A and the light transmitting regions 9a are formed by patterning a metal reflection layer made of Al on a transparent substrate 9b that will be described later. The light transmitting regions 9a in FIG. 2A correspond to light transmitting regions 9a1, 9a2, 9a3, 9a4, and the like in FIG. 2B, and the light shielding regions 9A in FIG. 2A correspond to light shielding regions 9A1, 9A2, 9A3, 9A4, and the like in FIG. 2B. That is, the light shielding film 9 has the plurality of light shielding regions 9A and the plurality of light transmitting regions 9a in the in-plane direction (within the xy plane) of the light shielding film 9. The plurality of light shielding regions 9A face the respective detectors 10A. The plurality of light transmitting regions 9a face the respective detectors 10a. The plurality of light shielding regions 9A (9A1 through 9A4) form a checkered pattern (see FIG. 2B). These light shielding regions 9A (9A1 through 9A4) may form a pattern other than a checkered pattern and may form, for example, a striped pattern.

The transparent substrate 9b is disposed on the light incident side of the light shielding film 9 and is made of a material such as $SiO_2$. The bandpass filter 9p is disposed on the light incident side of the transparent substrate 9b and selectively transmits only light having a wavelength in the vicinity of $\lambda_0$ of the incident scattered light 5.

The light 5 that enters the light detection device 13 passes through the bandpass filter 9p and the transparent substrate 9b and then reaches, as light 6A and 6a, the light shielding regions 9A in which a reflection film is formed and the light transmitting regions 9a from which a reflection film is removed. The light 6A is blocked by the light shielding regions 9A, but the light 6a transmits the light transmitting regions 9a and enters the light coupling layer 12. The light 6a that has entered the light coupling layer 12 passes through the low-refractive-index transparent layer 12a and then enters the high-refractive-index transparent layer 12b. The grating 12d is formed on upper and lower interfaces of the high-refractive-index transparent layer 12b, and guided light 6b is generated in a case where the pitch A of the grating 12d satisfies the formula 2:

$$\sin\theta = N - \frac{\lambda_0}{\Lambda} \qquad \text{formula 2}$$

In the formula 2, N is an effective refractive index of the guided light 6b and θ is an incident angle with respect to a normal to an incident surface (the xy surface). In FIG. 2A, θ=0 since light enters the incident surface in a direction perpendicular to the incident surface. In this case, the guided light 6b propagates in the x direction within the xz plane.

A component that passes through the high-refractive-index transparent layer 12b and enters a lower layer also enters all of the high-refractive-index transparent layers 12b on the lower layer side, and guided light 6c is generated on the same condition as the formula 2. Note that guided light that is generated in two layers is illustrated as representatives in FIG. 2A although guided light is actually generated in all of the high-refractive-index transparent layers 12b. The guided light 6c that is generated on the lower layer side also propagates in the x direction within the xz plane. The guided light 6b and 6c propagates while radiating light upward and downward at an angle θ (θ=0 in the example in FIG. 2A) with respect to the normal to the waveguide plane (the xy plane). Radiated light 6B1 and 6C1 thus radiated upward (toward the reflection film side) directly below the light shielding regions 9A is reflected by the light shielding regions 9A and becomes light 6B2 that travels downward along the normal to the reflection surface (the xy plane). Since the light 6B1, 6C1, and 6B2 satisfies the formula 2 with respect to the high-refractive-index transparent layer 12b, part of the light 6B1, 6C1, and 6B2 becomes the guided light 6b and 6c again. This guided light 6b and 6c also generates new radiated light 6B1 and 6C1. This cycle is repeated. As a whole, directly below the light transmitting regions 9a, a component that has not become guided light passes through the light coupling layer 12, enters the microlens 10b as transmitted light 6d, and is then detected by the detector 10a. Directly below the region 9A, a component that has become guided light is radiated, enters the microlens 10B as radiated light 6D, and is then detected by the detector 10A.

The light transmitting regions 9a correspond to the opening illustrated in FIG. 1B. Through the light transmitting regions 9a, light branches into light to be detected by detectors directly below the light transmitting regions 9a and light to be detected by detectors on the left and right. Assume that the amounts of light detected by detectors that face the light transmitting regions 9a1, 9a2, 9a3, and 9a4 illustrated in FIG. 2B are q1, q2, q3, and q4, respectively, and the amounts of light detected by detectors that face the light shielding regions 9A1, 9A2, 9A3, 9A4 illustrated in FIG. 2B are Q1, Q2, Q3, and Q4, respectively, the former four amounts of detected light are the amounts of detected light that has not become guided light, and the latter four amounts of detected light are the amounts of detected light that has become guided light. The amounts of light that has become guided light is not detected by the detector directly below the light transmitting region 9a1, and the amount of light that has not become guided light is not detected by the detector directly below the light shielding region 9A2. The amount of detected light that has become guided light at a detection position directly below the light transmitting region 9a1 is defined as Q0=(Q1+Q2+Q3+Q4)/4 (or Q0=(Q1+Q2)/2), and the amount of detected light that has not become guided light at a detection position directly below the light shielding region 9A2 is defined as q=(q1+q2+q3+q4)/4 (or q0=(q1+q2)/2). That is, an average of light amounts detected at detection positions directly below regions adjacent to a certain region (a light shielding region or a light transmitting region) in the x direction and/or the y direction is defined. By applying this definition to all regions, the amount of detected light that has not become guided light and the amount of detected light that has become guided light can be defined in all detection regions that constitute the light detector 10 (all of the detectors that constitute the light detector 10). The arithmetic circuit 11 defines the amount of detected light that has not become guided light and the amount of detected light that has become guided light in all of the detectors that constitute the light detector 10 as described above and then performs arithmetic processing such as generating an image by allocating a value of a ratio of these amounts calculated for each detector to a pixel corresponding to the detector.

Figure 3E:
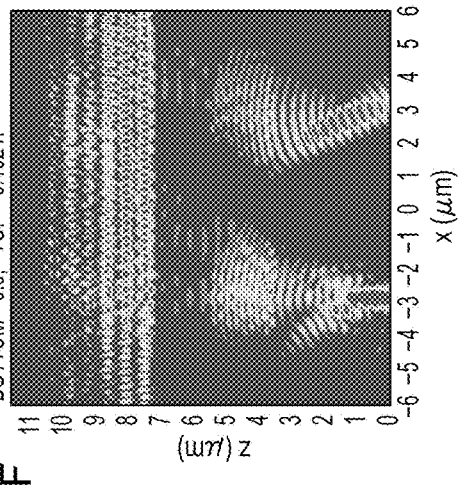
FIG. 3E is a diagram illustrating, in chronological order, electromagnetic analysis of how 1-pulse incident light passes through a light coupling layer and is then received by the detectors in First Embodiment.

Next, how 1-pulse-oscillated incident light passes through the light coupling layer 12 and is then received by the light detector 10 is described. FIG. 3A is the same cross-sectional view as FIG. 2A, and FIGS. 3B through 3H illustrate, in chronological order, results of electromagnetic analysis of a light intensity distribution using FDTD and are drawn corresponding to FIG. 3A. The width of each of the regions 9a and 9A in the x and y directions is 5.6 µm, the depth of the grating 12d in the z direction is 0.2 µm, the high-refractive-index transparent layer (the second transparent layer) is a $Ta_2O_5$ film, the thickness t1 of the high-refractive-index transparent layer in the z direction is 0.34 µm, the low-refractive-index transparent layer (the first transparent layer) is a $SiO_2$ film, and the thickness t2 of the low-refractive-index transparent layer in the z direction is 0.22 µm.

Figure 3F:
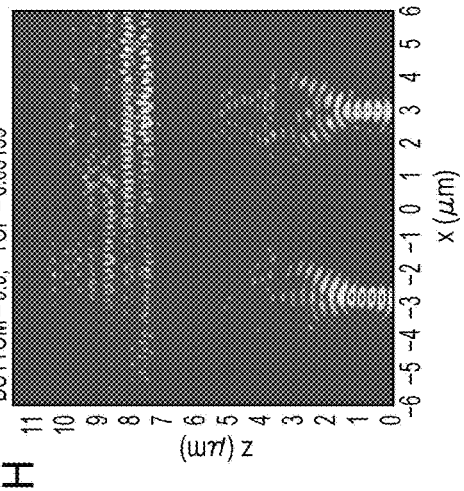
FIG. 3F is a diagram illustrating, in chronological order, electromagnetic analysis of how 1-pulse incident light passes through a light coupling layer and is then received by the detectors in First Embodiment.
Figure 3G:
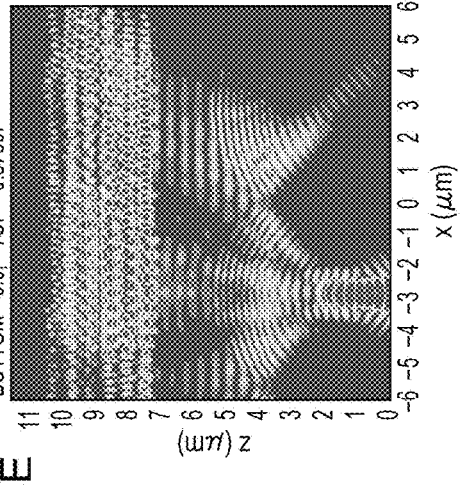
FIG. 3G is a diagram illustrating, in chronological order, electromagnetic analysis of how 1-pulse incident light passes through a light coupling layer and is then received by the detectors in First Embodiment.
Figure 3H:
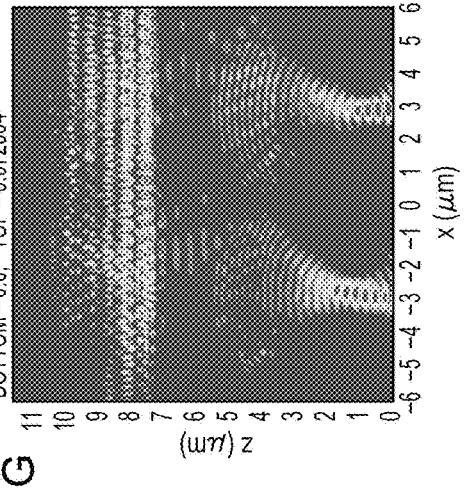
FIG. 3H is a diagram illustrating, in chronological order, electromagnetic analysis of how 1-pulse incident light passes through a light coupling layer and is then received by the detectors in First Embodiment.

In FIG. 3B, the light 6a having a wavelength $\lambda_0$ of 850 nm that has been pulse-oscillated so that a half width is 11 fs (3.3 µm when converted into a propagation distance) passes through the light transmitting regions 9a. In FIG. 3C, oscillation of the light 6a ends, and the guided light 6b and 6c that propagates in the stacked high-refractive-index transparent layers 12b is generated, and a component that has not become guided light passes through the light coupling layer 12 as it is and enters the microlens 10b (the light 6d). In FIG. 3D, the guided light 6b and 6c propagates to a region below the light shielding regions 9A while radiating the light 6B1 and 6C1 upward and downward. Meanwhile, the transmitted light 6d is collected onto the detector 10a by the microlens 10b. In FIG. 3E, the transmitted light 6d enters the detector 10a. Meanwhile, the radiated light 6B1 and 6C1 and the reflected light 6B2 form the radiated light 6D and enters the microlens 10B and is thus collected. In FIGS. 3F through 3H, the transmitted light 6d and the radiated light 6D are collected and enter the detectors 10a and 10A, respectively. The curve 14A in FIG. 4A illustrates a relationship between a value of P1/P0 and the coherence length of the incident light where P0 and P1 are total amounts of light detected by the detectors 10a and 10A, respectively. Note that the coherence length is one obtained by multiplying a pulse width (i.e., a coherence time) by light speed. Furthermore, the amount of detected light P1 is one obtained by doubling the amount of light received by the detector 10A that is a result of analysis in FIGS. 3A through 3H. This is because only a component radiated from the guided light 6b1 and the like is detected in the analysis, but actually, a component radiated from similar guided light 6b1' and the like propagated from an opposite side is also added (see FIG. 2B). The light amount ratio P1/P0 is a light amount ratio of a component coupled with guided light by a grating coupler (a light coupler using a grating such as the structure of the high-refractive-index transparent layer (the second transparent layer) 12b illustrated in FIG. 2A) and a component that is not coupled.

Figure 4B:
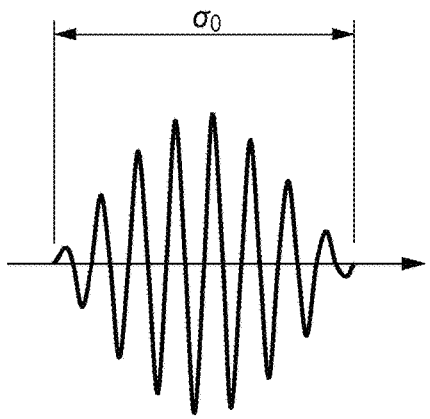
FIG. 4B is an explanatory view illustrating a pulse condition of a light source in FIG. 4A.
Figure 4C:
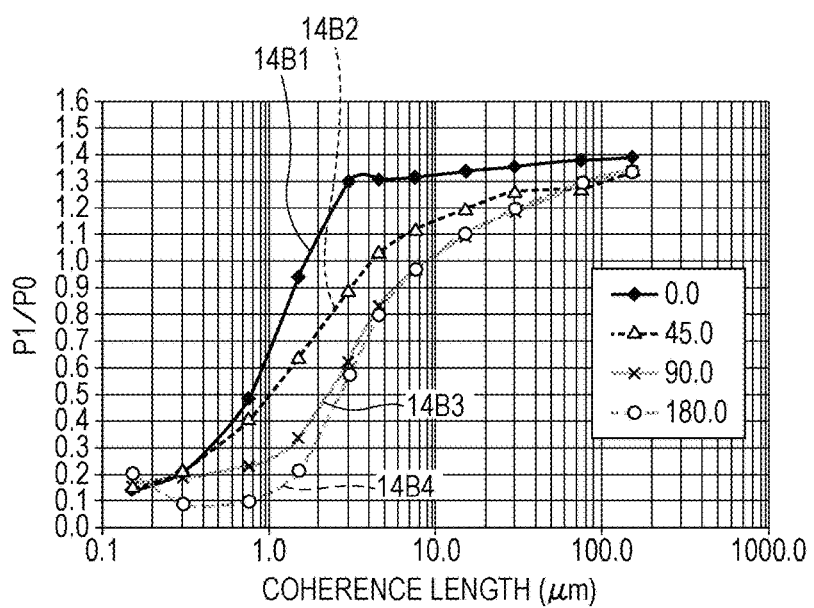
FIG. 4C is an explanatory view illustrating a relationship between a ratio P1/P0 of amounts of light detected by detectors and an effective coherence length (pulse width) of incident light on another pulse condition in First Embodiment.
Figure 4D:
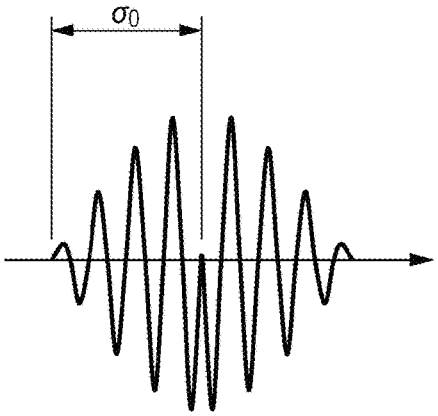
FIG. 4D is an explanatory view illustrating a pulse condition of a light source in FIG. 4C.

As is clear from FIG. 4A, the light amount ratio P1/P0 is small, specifically, approximately 0.2 when the coherence length is equal to or shorter than 1 µm, the light amount ratio P1/P0 is large, specifically, approximately 1.3 when the coherence length is equal to or longer than 10 µm, and the light amount ratio P1/P0 monotonically increases in accordance with an increase in the coherence length when the coherence length is between 1 µm and 10 µm. That is, the light amount ratio P1/P0 strongly depends on coherence (the degree of coherence) of incident light. The light amount ratio P1/P0 is small in a case of incoherent light such as solar light (a coherence length equal to or shorter than 1 µm), increases as the coherence of light increases, and is saturated in the case of partially coherent light (a coherence length equal to or longer than 10 µm). Note that the curve 14A illustrates a result obtained in a case where a light source oscillates a pulse on a pulse condition (condition A) illustrated in FIG. 4B. That is, the amplitude of the pulse forms an envelope of a Gaussian distribution, and a phase within a pulse width is uniform. In this case, coherence length $\sigma_0$=pulse width×light speed. Meanwhile, the curves 14B1 through 14B4 in FIG. 4C illustrate results obtained in a case where a pulse is oscillated on a pulse condition illustrated in FIG. 4D. That is, the amplitude of the pulse forms an envelope of a Gaussian distribution, but a phase changes by φ at a peak of the Gaussian distribution. The curves 14B1 through 14B4 illustrate results obtained on conditions that the phase difference φ is 0, π/4, π/2, and π, respectively. In this case, the coherence length is defined by $\sigma_0$=pulse width×light speed/2. Note that although the condition of φ=0 of the curve 14B1 is the same as the condition of the curve 14A, the property of the curve 14B1 is one obtained by almost halving the scale in the horizontal axis of the curve 14A because the definition of the coherence length $\sigma_0$ is different. As illustrated in FIG. 4C, a curve shifts to a longer coherence length side as the phase difference φ becomes larger. Statistically, a phase difference between adjacent wave trains is between 0 and π, but the curve 14A having a property doubling the scale in the horizontal axis of the curve 14B1 is considered an average property.

Note that as is clear from FIGS. 3E through 3H, the guided light 6b and 6c is not fully radiated in a range below the light shielding regions 9A and part thereof reaches a range of an adjacent light transmitting region in a state of guided light. Since a radiation loss coefficient (easiness of radiation of guided light) becomes larger as the depth of a grating becomes deeper, the amount of detected light P1 can be made larger and the degree of modulation of the light amount ratio P1/P0 can be further increased as the depth of the grating in a region below the light shielding region 9A is made deeper.

Figure 5A:
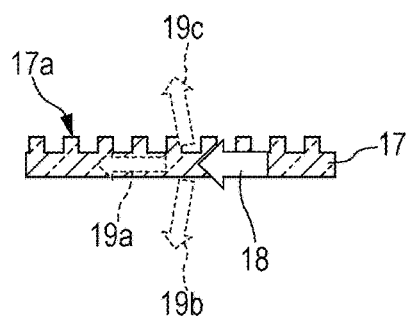
FIG. 5A is an explanatory view illustrating a relationship between input light and coupled light in a grating coupler.
Figure 5B:
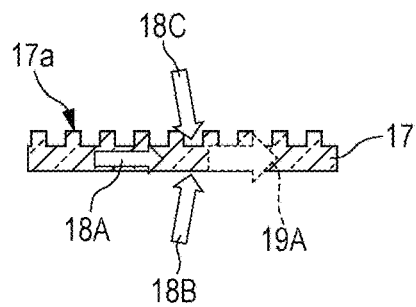
FIG. 5B is an explanatory view illustrating a relationship between input light and coupled light in the grating coupler.
Figure 5C:
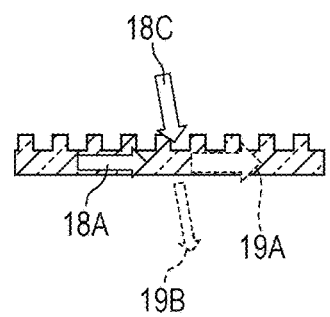
FIG. 5C is an explanatory view illustrating a relationship between input light and coupled light in the grating coupler.
Figure 5D:
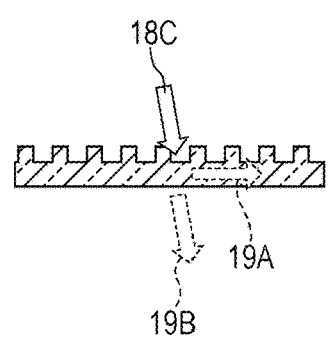
FIG. 5D is an explanatory view illustrating a relationship between input light and coupled light in the grating coupler.

FIGS. 5A through 5D illustrate a relationship between input light and coupled light in the grating coupler. In FIGS. 5A through 5D, a grating 17a is formed on a waveguide layer 17 and functions as a grating coupler as a whole. The waveguide layer 17 corresponds to the second transparent layer 12b in the present embodiment. In FIG. 5A, input light (guided light 18 that propagates in the waveguide layer 17) is separated into three kinds of coupled light, i.e., guided light 19a and radiated light 19b and 19c by the grating coupler. According to a reciprocity theorem in a waveguide theory, in a case where waves propagating in a direction reverse to the three kinds of coupled light in FIG. 5A, i.e., guided light 18A and incident light 18B and 18C are concurrently input (triple pumping), guided light 19A is generated at 100% efficiency, as illustrated in FIG. 5B. Meanwhile, in a case where waves propagating in a direction reverse to two kinds of coupled light of the three kinds of coupled light in FIG. 5A, i.e., guided light 18A and incident 18C are concurrently input (double pumping), guided light 19A and transmitted light 19B are generated, and the amount of the guided light 19A is reduced, as illustrated in FIG. 5C. Meanwhile, in a case where a wave propagating in a direction reverse to a single kind of coupled light of the three kinds of coupled light in FIG. 5A, i.e., only incident light 18C is input (single pumping), guided light 19A and transmitted light 19B are generated, and the amount of guided light 19A is further reduced, as illustrated in FIG. 5D. That is, the input efficiency in generation of the guided light 19A becomes smaller in the order of FIGS. 5B, 5C, and 5D.

Figure 6A:
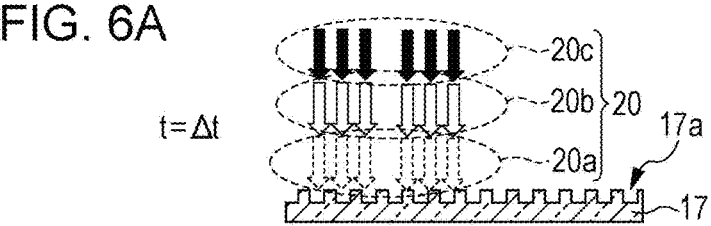
FIG. 6A is an explanatory view illustrating a principle of strong dependence of the light amount ratio P1/P0 on the effective coherence length of the incident light in First Embodiment.
Figure 6B:
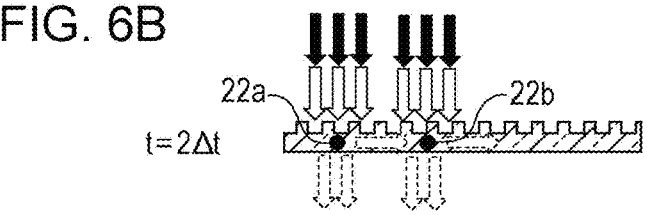
FIG. 6B is an explanatory view illustrating a principle of strong dependence of the light amount ratio P1/P0 on the effective coherence length of the incident light in First Embodiment.
Figure 6C:
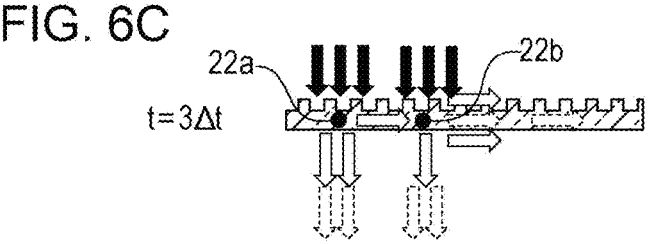
FIG. 6C is an explanatory view illustrating a principle of strong dependence of the light amount ratio P1/P0 on the effective coherence length of the incident light in First Embodiment.
Figure 6D:
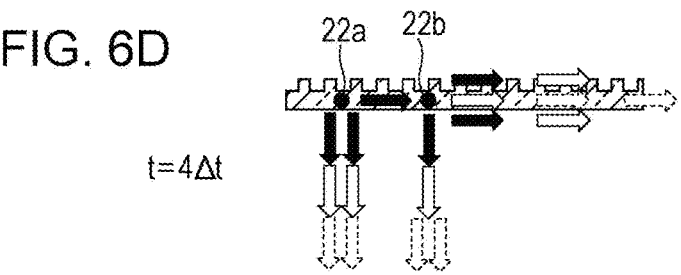
FIG. 6D is an explanatory view illustrating a principle of strong dependence of the light amount ratio P1/P0 on the effective coherence length of the incident light in First Embodiment.
Figure 6E:
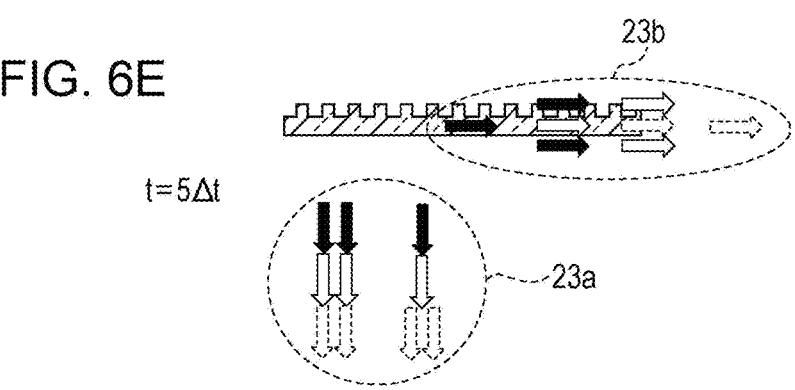
FIG. 6E is an explanatory view illustrating a principle of strong dependence of the light amount ratio P1/P0 on the effective coherence length of the incident light in First Embodiment.
Figure 6F:
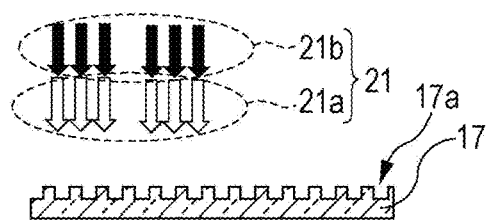
FIG. 6F is an explanatory view illustrating a principle of strong dependence of the light amount ratio P1/P0 on the effective coherence length of the incident light in First Embodiment.
Figure 6G:
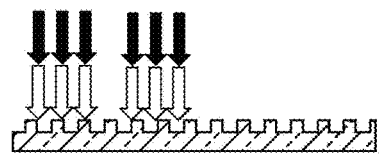
FIG. 6G is an explanatory view illustrating a principle of strong dependence of the light amount ratio P1/P0 on the effective coherence length of the incident light in First Embodiment.
Figure 6H:
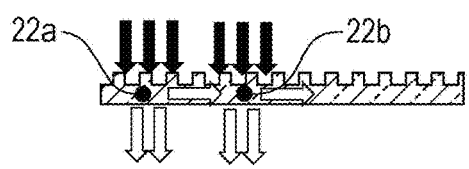
FIG. 6H is an explanatory view illustrating a principle of strong dependence of the light amount ratio P1/P0 on the effective coherence length of the incident light in First Embodiment.
Figure 6I:
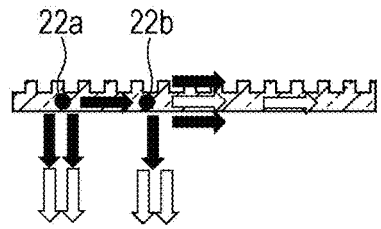
FIG. 6I is an explanatory view illustrating a principle of strong dependence of the light amount ratio P1/P0 on the effective coherence length of the incident light in First Embodiment.
Figure 6J:
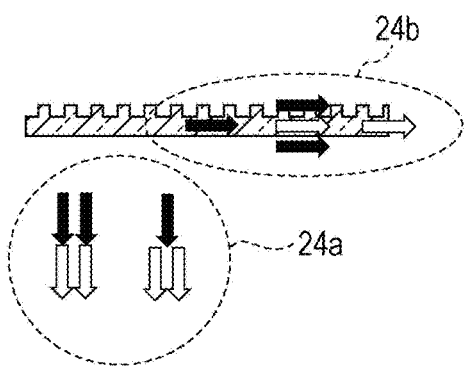
FIG. 6J is an explanatory view illustrating a principle of strong dependence of the light amount ratio P1/P0 on the effective coherence length of the incident light in First Embodiment.

FIGS. 6A through 6J illustrate a principle of strong dependence of the light amount ratio P1/P0 on a coherence length of incident light. In FIGS. 6A through 6J, the grating 17a is formed on the waveguide layer 17 and functions as a grating coupler as a whole. FIGS. 6A through 6E illustrate a case where the coherence length of the incident light is long and illustrate how a single wave train 20 that is divided into three stages, i.e., arrows 20a (the broken line), 20b (the solid line), and 20c (blackened out) propagates and is branched with passage of time. FIGS. 6F through 6J illustrate a case where the coherence length of the incident light is short and illustrate how a single wave train 21 that is divided into two stages, i.e., arrows 21a (the solid line) and 21b (blackened out) propagates and is branched with passage of time. In FIG. 6A, the long wave train 20 enters the grating coupler, and in FIG. 6B, weak guided light (each indicated by a single broken-line arrow) is generated by single pumping at two positions 22a and 22b, and remaining light passes through the grating coupler (each indicated by two broken-line arrows). In FIG. 6C, the wave train 20 is separated into weak guided light (indicated by a single broken-line arrow) and strong transmitted light (indicated by two broken-line arrows) by single pumping at the position 22a. Furthermore, the wave train 20 is separated into strong guided light (indicated by a single broken-line arrow and two solid-line arrows) and weak transmitted light (indicated by a single solid-line arrow) by double pumping at the position 22b. Pumping at the position 22b is double pumping because guided light that propagates from the left side is added to the incident light from an upper side. In FIG. 6D, the wave train 20 is separated into weak guided light (indicated by a single blackened-out arrow) and strong transmitted light (indicated by two blackened-out arrows) by single pumping at the position 22a, and the wave train 20 is separated into strong guided light (indicated by a single solid-line arrow and two blackened-out arrows) and weak transmitted light (indicated by a single blackened-out arrow) by double pumping at the position 22b. In FIG. 6E, propagation of the guided light and the transmitted light in FIG. 6D continues. When the light amount ratio P1/P0 is estimated on the basis of the number of arrows, P1/P0=8/10=0.80 since the number of arrows (23b) that indicate guided light is 8 and the number of arrows (23a) that indicate transmitted light is 10. Meanwhile, in FIGS. 6F and 6G, the short wave train 21 enters the grating coupler. In FIG. 6H, weak guided light (each indicated by a single solid-line arrow) is generated by single pumping at two positions 22a and 22b, and remaining light passes through the grating coupler (each indicated by two solid-line arrows). In FIG. 6I, the wave train 21 is separated into weak guided light (indicated by a single blackened-out arrow) and strong transmitted light (indicated by two blackened-out arrows) by single pumping at the position 22a. Furthermore, the wave train 21 is separated into strong guided light (indicated by a single solid-line arrow and two blackened-out arrows) and weak transmitted light (indicated by a single blackened-out arrow) by double pumping at the position 22b. Pumping at the position 22b is double pumping because guided light that propagates from the left side is added to incident light from an upper side. In FIG. 6J, propagation of the guided light and the transmitted light in FIG. 6I continues. When the light amount ratio P1/P0 is estimated on the basis of the number of arrows, P1/P0=5/7=0.71 since the number of arrows (24b) that indicate guided light is 5 and the number of arrows (24a) that indicate transmitted light is 7. This shows that in a case where incident light has a longer coherence length, the probability of occurrence of double pumping is higher, and therefore the light amount ratio P1/P0 is higher.

Figure 7:
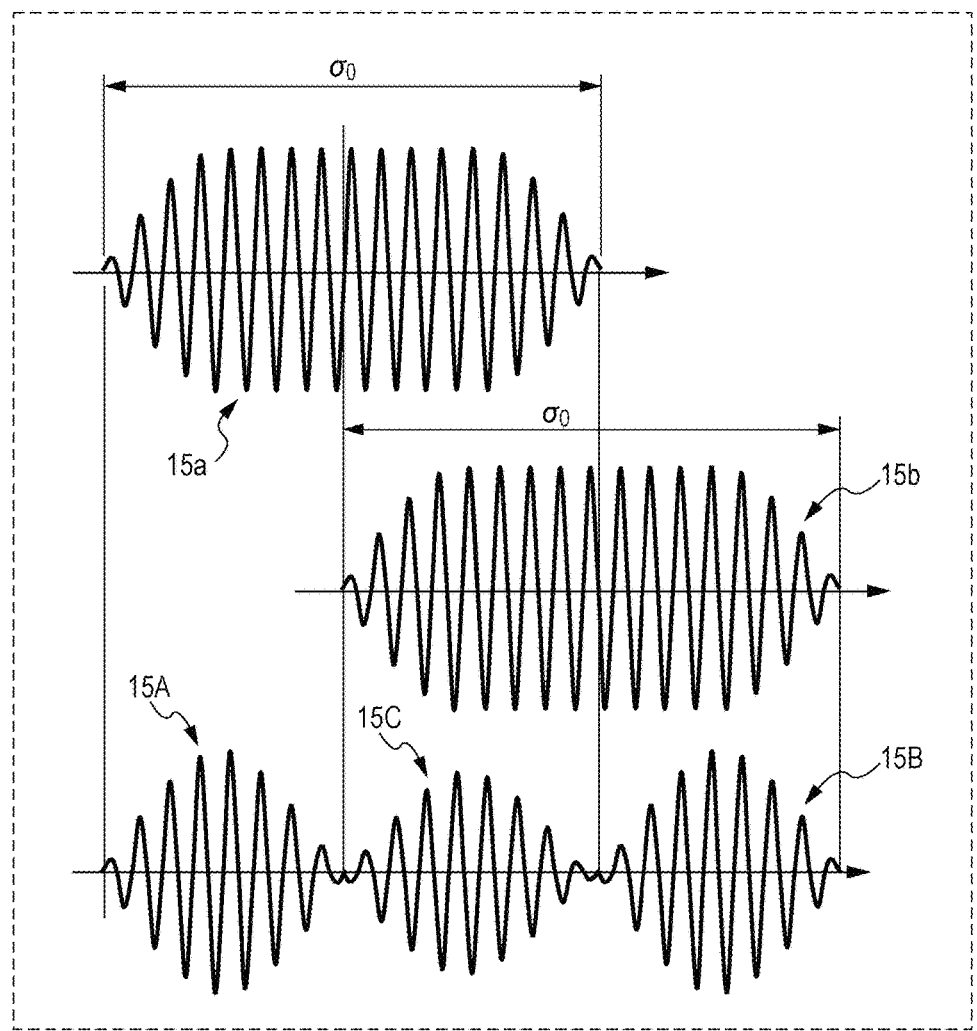
FIG. 7 is an explanatory view illustrating wave trains that enter an opening of a light detector.

FIG. 7 illustrates a wave train that enters the opening 9a illustrated in FIG. 1B. Since the light source 2 emits light of a constant coherence length $\sigma_0$, all of wave trains 15a and 15b that enter the opening 9a have the same coherence length $\sigma_0$ assuming that the coherence length does not change in the subject 4. However, the wave trains 15a and 15b enter the opening 9a at different timings due to scattering. As illustrated in FIG. 7, in a case where the two wave trains 15a and 15b (a wave train that has the same coherence length and a different phase follows the wave trains 15a and 15b) are successively incident while phases thereof are randomly shifted from each other, the wave trains 15a and 15b interfere with each other to form three wave trains 15A, 15B, and 15C. The wave train 15C is a wave train that is generated by overlapping and interference between the wave trains 15a and 15b. The wave trains 15A and 15B are remaining parts of the wave train 15a and the wave train 15b that do not overlap each other. The wave trains 15A, 15B, and 15C have the same wavelength, but there is no correlation in phase among the wave trains 15A, 15B, and 15C, and the length of each wave train is shorter than the original length $\sigma_0$. The expanse of wavelength (longitudinal mode width) of the composite waves (the wave trains 15A, 15B, and 15C) is the same as that of the original wave trains 15a and 15b. That is, a coherence length defined by time coherence does not change (see FIGS. 5A through 5D). Meanwhile, in a case where a coherence length is defined as continuity of waves, i.e., a length of waves having a continuous phase, the coherence length of the composite wave is shorter. Hereinafter, a coherence length defined in this meaning is referred to as an "effective coherence length", and a coherence length defined by time coherence is referred to as a "coherence length" so as to be distinguished from the "effective coherence length". Without the effect illustrated in FIG. 7, the effective coherence length is equal to the coherence length. The effective coherence length is always equal to or shorter than the coherence length. If the coherence length becomes shorter, the effective coherence length also becomes shorter. Furthermore, also in a case where spatial coherence deteriorates, the effective coherence length becomes shorter. The "coherence length" in the description of FIGS. 3A through 3H, FIGS. 4A through 4D, and FIGS. 6A through 6J is used in the meaning of an effective coherence length. That is, the light amount ratio P1/P0 in FIG. 4A strongly depends on an effective coherence length of incident light.

Figure 8A:
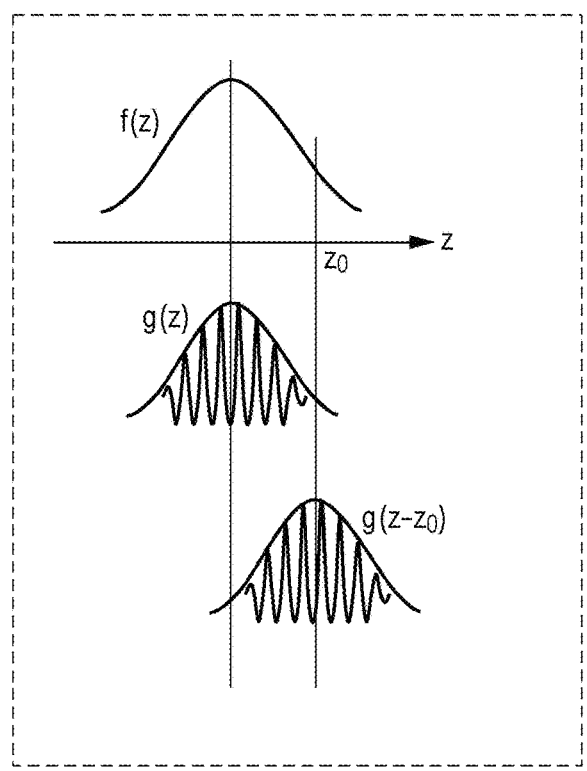
FIG. 8A is an explanatory view illustrating a relationship between a variation of optical path lengths of incident light that enters the opening of the light detector and attenuation of the effective coherence length.
Figure 8B:
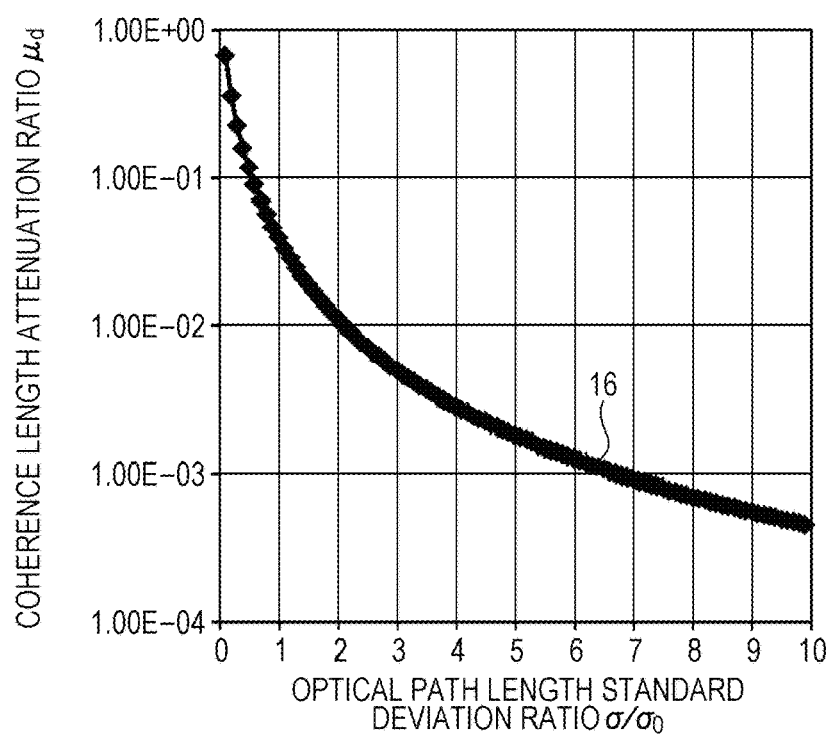
FIG. 8B is a diagram illustrating a relationship between an attenuation ratio $\mu_d$ of the effective coherence length and a ratio $\sigma/\sigma_0$ of an optical path length standard deviation $\sigma$ to the effective coherence length $\sigma_0$.

FIGS. 8A and 8B are explanatory views illustrating how a variation in optical path length (phase) of light that enters the opening 9a is related to attenuation of an effective coherence length. Light beams that enter the opening 9a can be statistically handled by using a light beam tracing technique such as a Monte Carlo method on the assumption of continuous oscillation. For example, assume that a large number of light beams are emitted from the light source 2, n light beams enter the opening 9a, and the optical path length of a k-th light beam of the n light beams is $s_k$ (k=1, 2, . . . n). As illustrated in FIG. 8A, z is a distance in a propagation axis direction, a statistical distribution of the optical path length $s_k$ is given by f (z), and an incident intensity waveform of the light beam (a temporal change of a light intensity multiplied by light speed and converted into a distance unit) is given by g (z). When the attenuation principle of the effective coherence length in FIG. 7 is statistically processed, probability $\mu_d$ that a wave train g $(z-z_0)$ is within the same wave train as the standard wave train g (z) is given by the formula 3, and $\mu_d$ represents an attenuation ratio of the effective coherence length. Note that g (z) is defined by the formula 4, and $\sigma_0$ is a coherence length of light emitted by the light source 2. The formula 5 holds where m and $\sigma$ are an average and a standard deviation of optical path lengths, and f (z) is a normal distribution.

$$\mu_d(\sigma, \sigma_0) = \int_{-\infty}^{+\infty} \left[ \int_{-\infty}^{+\infty} f(z_0)g(z)g(z-z_0)dz_0 \right] dz \quad \text{formula 3}$$

$$g(z) = e^{-\frac{z^2 \ln 2}{(\sigma_0/2)^2}} \quad \text{formula 4}$$

$$f(z) = \frac{1}{\sqrt{2\pi}\,\sigma} e^{-\frac{(z-m)^2}{2\sigma^2}} \quad \text{formula 5}$$

The curve 16 in FIG. 8B is a calculation result indicating a relationship between the attenuation ratio $\mu_d$ and a ratio $\sigma/\sigma_0$ of the optical path length standard deviation $\sigma$ to the effective coherence length $\sigma_0$. The curve 16 shows that the attenuation ratio $\mu_d$ becomes smaller as the ratio $\sigma/\sigma_0$ increases. Note that in a case where f (z) is not a normal distribution, the curve 16 exhibits a different property.

The relationships in FIGS. 8A and 8B are established in the case of continuous oscillation, but can be approximately established even in a case of pulse oscillation as long as a variation of optical path lengths and a pulse length (a value obtained by multiplying a pulse time width by light speed) are approximately the same. Note that from the definition of an effective coherence length, in a case where a phase difference between adjacent wave trains is small, these wave trains should be regarded as a single wave train, but this is ignored in the formula 3. Accordingly, the influence of attenuation of the effective coherence length is excessively handled in the relationships in FIGS. 8A and 8B, but the following discussion is based on the relationships in FIGS. 8A and 8B.

Figure 9A:
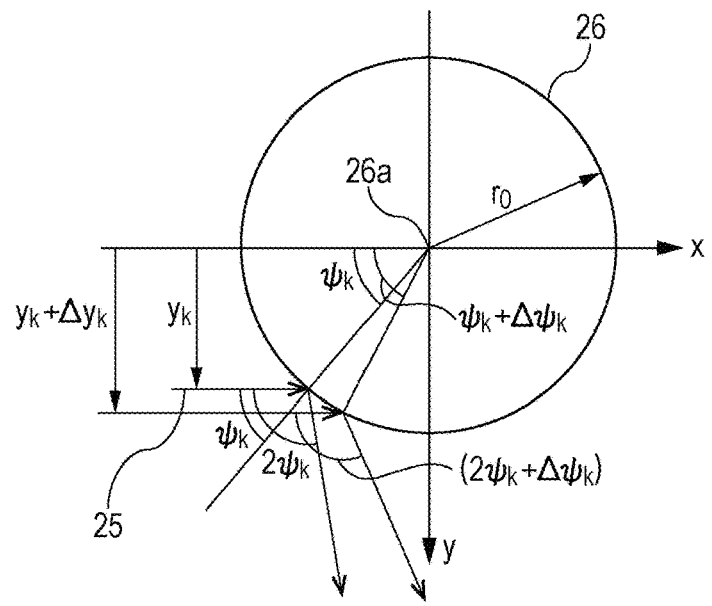
FIG. 9A is an explanatory view illustrating a principle of a change of a coherence length in a subject.
Figure 9B:
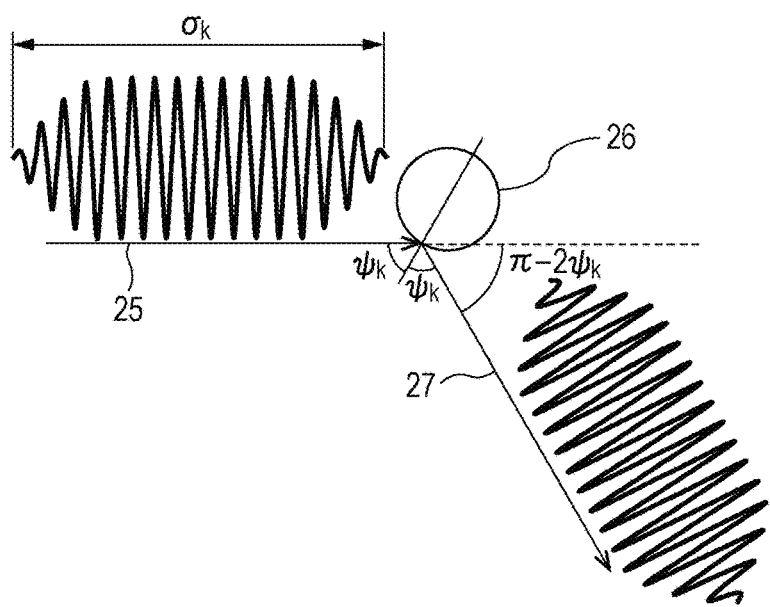
FIG. 9B is an explanatory view illustrating a principle of a change of a coherence length in a subject.
Figure 9C:
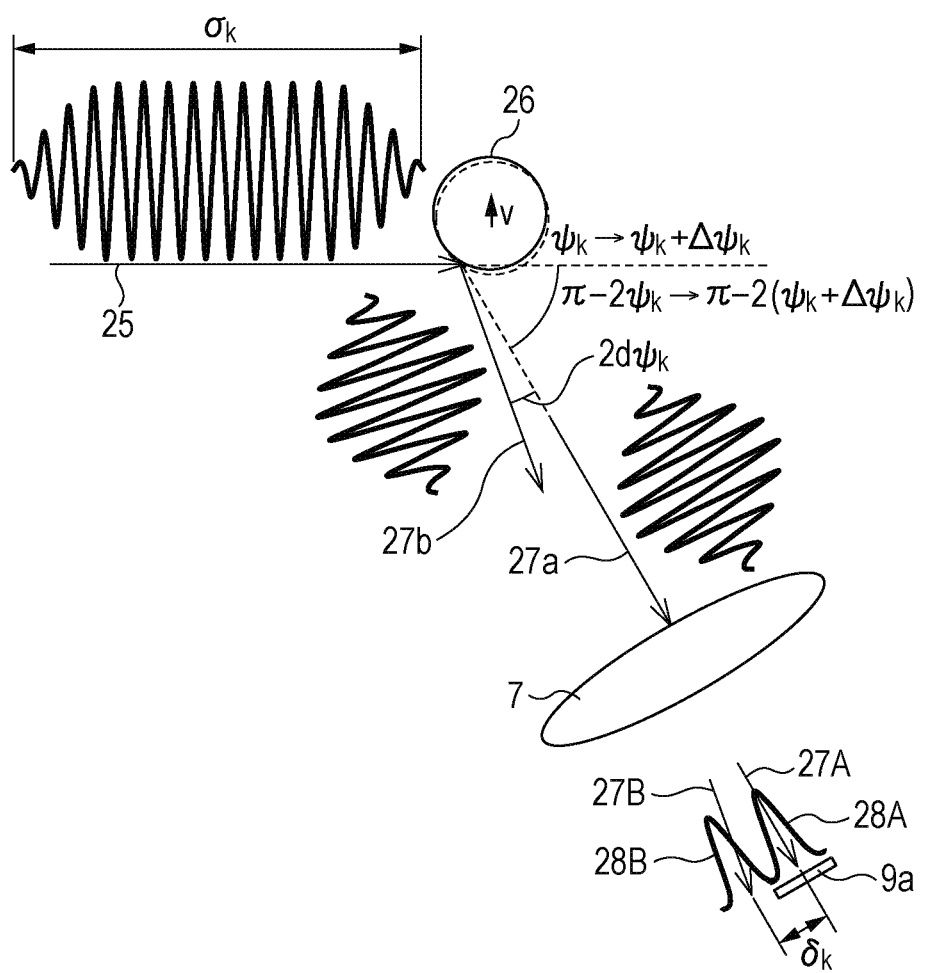
FIG. 9C is an explanatory view illustrating a principle of a change of a coherence length in a subject.

FIGS. 9A through 9C are explanatory views illustrating a principle of a change of a coherence length in the subject 4. Although the models in FIGS. 8A and 8B indicate a deterioration of effective coherence (a deterioration of spatial coherent), the models in FIGS. 9A through 9C indicate a deterioration of time coherence. Assume that light having a wavelength $\lambda_0$ is scattered n times in a subject having a refractive index $n_0$, and the light enters a spherical reflector 26 having a radius of $r_0$ by k-th scattering as illustrated in FIG. 9A. The coherence length of the light is $\sigma_k$, the position in the y-axis direction at which the light enters the spherical reflector 26 is $y_k$, an incident angle with respect to a normal to a surface of the spherical reflector 26 is $\varphi_k$, and the x-axis is parallel with a light propagation direction. It is assumed that entry and reflection of the light occur within the same plane including a center 26a of the sphere. In a case where the position of the wave train 25 in the y-axis direction changes from $y_k$ to $y_k+\Delta y_k$, the angle $\varphi_k$ changes to $\varphi_k+\Delta\varphi_k$. As illustrated in FIG. 9B, in a case where the reflector 26 is still, there is no change in coherence length of the wave train 27 after reflection. As illustrated in FIG. 9C, in a case where the reflector 26 moves within the xy plane while the wave train 25 is being reflected by the reflector 26 (a y component of movement speed is v), the wave train 25 is separated into two wave trains, i.e., a wave train 27a and a wave train 27b after reflection. The wave trains 27a and 27b exit the subject to an outside, passes through the light collecting lens 7 having a focal length f to become convergent light 27A and 27B, and are collected onto a detection pixel surface 9a to form light collection spots (intensity distributions 28A and 28B) whose centers are spaced away from each other by $\delta_k$. The diameter of the light collection spots is given by $\lambda_0/NA$ where NA is a numerical aperture of the light collecting lens 7. An amount $\Delta y_k$ of change during reflection of the wave train by the reflector 26 is given by the formula 6 (c is light speed):

$$\Delta y_k = v\sigma_k/c \quad \text{formula 6}$$

The relationships of the formulas 7, 8, and 9 are established among $g_k$, $\varphi_k$, and $\delta_k$ where $g_k$ is the cosine of a scattering angle in the k-th scattering and $n_0$ is a refractive index of the subject.

$$g_k = \cos(\pi - 2\varphi_k) = \cos(2\varphi_k) \quad \text{formula 7}$$

$$\cos\varphi_k = \sqrt{(2g_k - 1 + \sqrt{5 - 4g_k})/2} \quad \text{formula 8}$$

$$2\Delta\varphi_k n_0 \cdot f = \delta_k \quad \text{formula 9}$$

Meanwhile, $y_k$ and the angle $\varphi_k$ have a relationship of the formula 10, and $\Delta\varphi_k$ is given by the formula 11.

$$y_k = r_0 \sin\varphi_k \quad \text{formula 10}$$

$$\Delta\varphi_k = \frac{dy_k}{r_0 \cos\varphi_k} = \frac{v\sigma_k}{cr_0 \cos\varphi_k} \quad \text{formula 11}$$

In a case where the interval $\delta_k$ between the centers of the light collection spots is larger than a spot diameter ($\lambda_0/NA$), it is considered that no interference occurs between the two spots, the two wave trains 27a and 27b (or 27A and 27B) are separated from each other, and the coherence length is divided into two parts. Accordingly, the number of divisions of the wave train caused by the k-th scattering is expressed by $2\Delta_k$ by using $\Delta_k$ given by the formula 12, and a coherence length in a (k+1)th scattering is given by the formula 13.

$$\Delta_k = \frac{\delta_k}{\lambda_0/NA} = \frac{2n_0 \Delta\varphi_k \cdot f}{\lambda_0/NA} = \frac{2n_0 v\sigma_k f \cdot NA}{\lambda_0 cr_0 \sqrt{(2g_k - 1 + \sqrt{5 - 4g_k})/2}} \quad \text{formula 12}$$

$$\sigma_{k+1} = \sigma_k/2^{\Delta_k} \quad \text{formula 13}$$

Since scattering is repeated n times in the subject 4, an attenuation ratio $\mu_i$ of the coherence length (a ratio of a final coherence length $\sigma_n$ to an initial coherence length $\sigma_0$) is given by the formula 14.

$$\mu_i = \sigma_n/\sigma_0 = 2^{-\Sigma_{k=1}^{n} \Delta_k} \quad \text{formula 14}$$

In a case where the subject 4 is a biological object, it is said that an anisotropic scattering coefficient is 0.9. This value corresponds to a condition of a grain size parameter ($2\pi \times$reflector radius/wavelength) to 1 in Mie scattering of a dielectric sphere. Based on this condition, the value can be regarded as reflector radius to 0.2×wavelength. For example, $\Delta_k$ is given by the formula 15 on the assumption that f=200 mm, NA=0.1, v=10 mm/s, c=3×10$^{11}$ mm/s, $\sigma_0$=6 mm, $\lambda_0$=0.85×10$^{-3}$ mm, and $n_0$=1.37 (condition D).

$$\Delta_k = \frac{0.072}{\sqrt{(2g_k - 1 + \sqrt{5 - 4g_k})/2}} \quad \text{formula 15}$$

$\Delta_k$ becomes a value of approximately 0.1, and the coherence length decreases almost by half after scattering is repeated approximately ten times.

In the models in FIGS. 9A through 9C, forward scattering corresponds to $2\varphi_k > \pi/2$, and backscattering corresponds to $2\varphi_k < \pi/2$. According to the formula 11, $\Delta\varphi_k$ is large in a case of $2\varphi_k > \pi/2$ (forward scattering), but $\Delta\varphi_k$ is small in a case of $2\varphi_k < \pi/2$ (backscattering). Accordingly, according to the formula 12 and the formula 13, the coherence length is easy to deteriorate in a case where forward scattering is performed many times, and the coherence length is hard to deteriorate in a case where backscattering is performed many times.

Figure 10B:
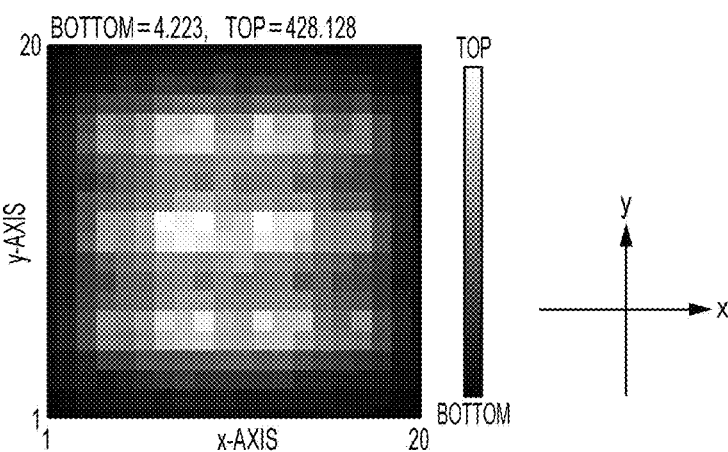
FIG. 10B is a diagram illustrating a detected light intensity distribution in the result calculated by a light beam tracing technique using a Monte Carlo method on the assumption that a subject is a human head.
Figure 10C:
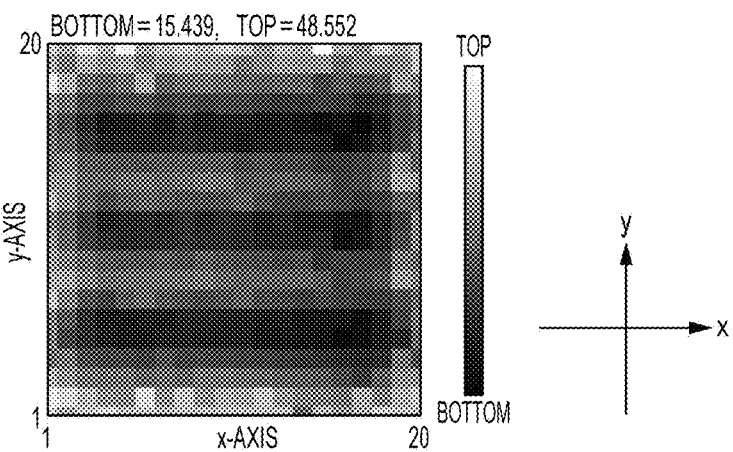
FIG. 10C is a diagram illustrating an optical path length average distribution in the result calculated by a light beam tracing technique using a Monte Carlo method on the assumption that a subject is a human head.
Figure 10D:
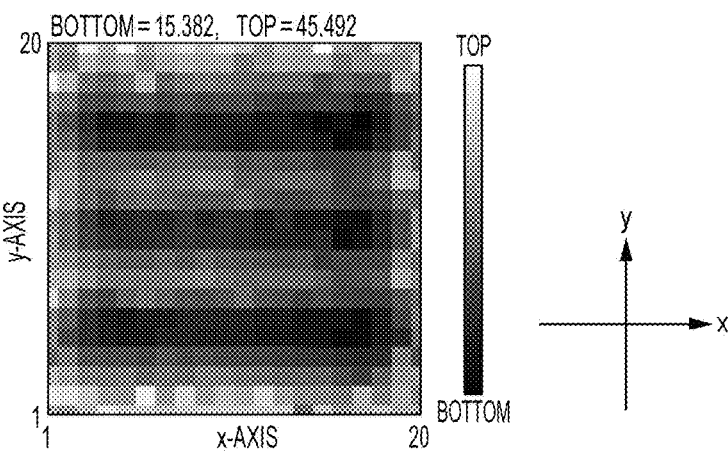
FIG. 10D is a diagram illustrating an optical path length standard deviation distribution in the result calculated by a light beam tracing technique using a Monte Carlo method on the assumption that a subject is a human head.
Figure 10E:
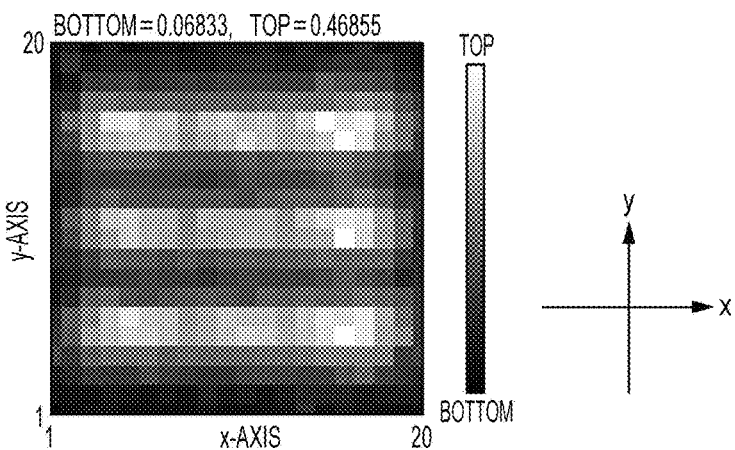
FIG. 10E is a diagram illustrating a distribution of coherence length attenuation in the result calculated by a light beam tracing technique using a Monte Carlo method on the assumption that a subject is a human head.
Figure 10F:
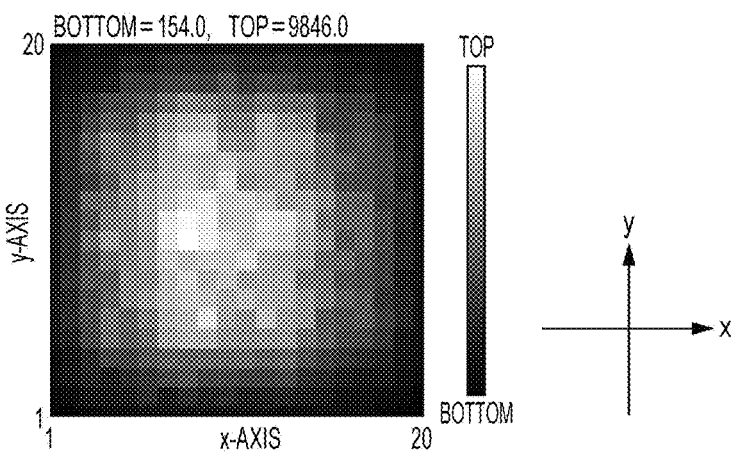
FIG. 10F is a distribution diagram obtained by multiplying values in respective regions in FIG. 10D by values in respective regions in FIG. 10B in the result calculated by a light beam tracing technique using a Monte Carlo method on the assumption that a subject is a human head.
Figure 10G:
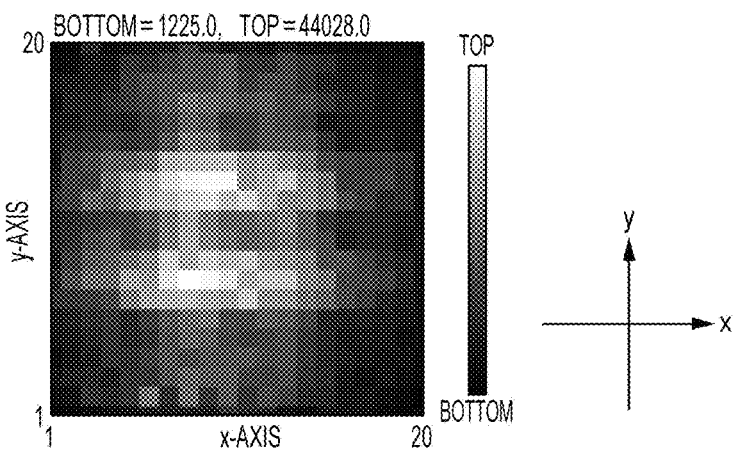
FIG. 10G is a distribution diagram obtained by dividing values in respective regions in FIG. 10F by values in respective regions in FIG. 10E in the result calculated by a light beam tracing technique using a Monte Carlo method on the assumption that a subject is a human head.
Figure 10H:
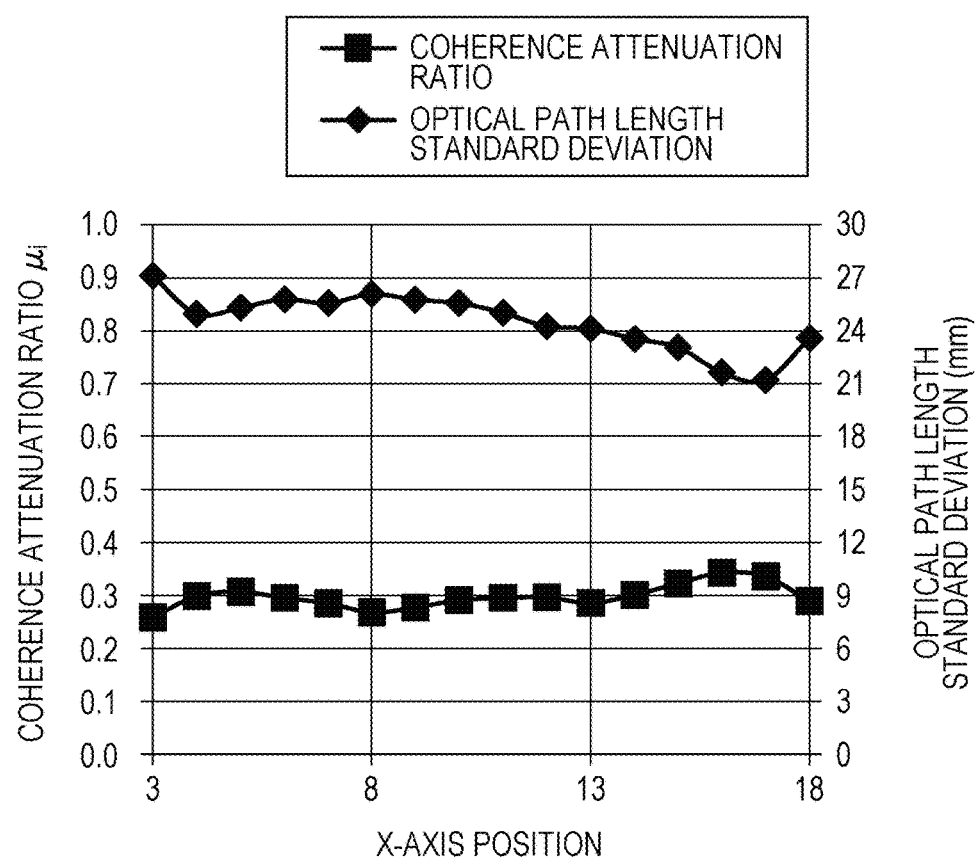
FIG. 10H is a diagram illustrating a distribution, on an x-axis, of averages of y-axis components of FIGS. 10D and 10E in the result calculated by a light beam tracing technique using a Monte Carlo method on the assumption that a subject is a human head.

FIGS. 10A through 10H are diagrams illustrating a result calculated by a light beam tracing technique using a Monte Carlo method on the assumption that a human head is used as a subject. FIG. 10A illustrates an overall optical arrangement and light beam tracing, and FIGS. 10B through 10G illustrates a result of analysis of an image 8b at a detection position that is divided into 20×20 regions. FIG. 10B illustrates a light intensity distribution, FIG. 10C illustrates an optical path length average distribution, FIG. 10D illustrates an optical path length standard deviation distribution, FIG. 10E illustrates a distribution of coherence length attenuation in the subject (a result of calculation of the formula 14), FIG. 10F illustrates a distribution obtained by multiplying values in respective regions in FIG. 10D by values in respective regions in FIG. 10B, FIG. 10G illustrates a distribution obtained by dividing values in respective regions in FIG. 10F by values in respective regions in FIG. 10E, and FIG. 10H illustrates a distribution of averages of y-axis components of FIGS. 10D and 10E on the x-axis in a range from a region 3 to a region 18 in the y-axis direction (a range from a region 3 to a region 18 in the x-axis direction is displayed). The human head is made up of a scalp 4a, a skull 4b, a CFS layer 4c, a gray matter 4d, and a white matter 4e. Table illustrates absorption coefficients (1/mm), scattering coefficients (1/mm), anisotropic scattering parameters, film thicknesses (mm) of the respective parts.

TABLE

| | absorption coefficient μa | scattering coefficient μs | anisotropic scattering parameter g | film thickness (mm) |
|---|---|---|---|---|
| scalp | 0.030 | 0.73 | 0.90 | 2.0 |
| skull | 0.012 | 1.80 | 0.90 | 4.0 |
| CFS layer | 0.002 | 0.30 | 0.90 | 1.0 |
| Gray matter | 0.036 | 2.30 | 0.90 | 40.0 |
| White matter | 0.014 | 9.10 | 0.90 | 40.0 |

As illustrated in FIG. 10A, the gray matter 4d and the white matter 4e are at the same depth and located in negative and positive regions of the x-axis, respectively. An analysis region is 40 mm×40 mm in the xy direction and 47 mm in the z direction, and light beams that propagate out of this region is excluded from calculation. It is assumed that incident light 3 perpendicularly enters a surface of the scalp 4a at 3×3 positions that are spaced away from each other by 10 mm in both x and y directions. An image 8b on an image formation plane is calculated from light beams that are taken in on conditions that the light collecting lens 7 is placed away by 1000 mm from the surface of the scalp 4a and an object-side numerical aperture (=sin α) is 0.1 (other conditions are the same as the condition D). The reason why a peripheral portion of FIG. 10B is dark (light intensity is small) is that light beams out of the analysis region are excluded from calculation. In FIG. 10B, a portion close to the light incident positions is bright (a light intensity is high). In FIG. 10C, a portion close to the light incident positions is dark (an optical path length is short). In FIGS. 10B, 10C, and 10D, a left half (x<0, the gray matter 4d side) looks slightly brighter than a right half, but is not clearly distinguishable. In FIG. 10E, a right half (x>0, the white matter 4e side) looks slightly brighter (coherence attenuation is smaller) than a left half. As a result of averaging excluding the peripheral portion, an average of optical path length standard deviations in FIG. 10D is approximately 26 mm in the left half and is approximately 21 mm in the right half, and an average of coherence length attenuation ratios in FIG. 10E is approximately 0.29 in the left half and is approximately 0.34 in the right half (see FIG. 10H). In FIGS. 10F and 10G, the left half (x<0) clearly looks brighter than the right half, reflecting a structural difference between the gray matter 4d and the white matter 4e.

Considering FIGS. 8A and 8B, FIGS. 9A through 9C, and FIGS. 10A through 10H together, the following can be said in FIG. 4A. That is, assume that a coherence length at the time of emission from the light source is 6 mm, the coherence length attenuates to 6.0×0.29=1.74 mm in the left half (the gray matter 4d side) and to 6.0×0.34=2.04 mm in the right half (the white matter 4e side) due to scattering in the subject according to FIG. 10E. Furthermore, according to FIG. 10D, the variation of optical path lengths is σ/σ$_0$=26/1.74=14.9 in the left half and is σ/σ$_0$=21/2.04=10.2 in the right half (see FIG. 4A). Accordingly, according to FIG. 8B, the effective coherence length attenuation ratio is 0.00020 in the left half and is 0.00043 in the right half. Accordingly, the effective coherence length of the detected light is 6 mm×0.00020=1.2 µm in the left half and is 6 mm×0.00043=2.6 µm in the right half. It is found that detected signals whose P1/P0 values are 0.3 and 0.6 are obtained from an intersection of a straight line 14*a* indicative of an effective coherence length of 1.2 µm and the curve 14A and an intersection of a straight line 14*b* indicative of an effective coherence length of 2.6 µm and the curve 14A in FIG. 4A. This shows that a distribution of the gray matter 4*d* and the white matter 4*e* that are behind the skull 4*b* can be detected by the detected signals P1/P0 detected by the light detection device 13 according to the present embodiment. A distribution of the detected signals P1/P0 is similar to those in FIGS. 10F and 10G, and the left half (x<0) and the right half can be distinguished from each other (the left half is smaller than the right half). Note that detection may be performed so that the positions of the straight lines 14*a* and 14*b*, i.e., effective coherence lengths of the detected light are on the left and right of a fluctuating portion (a range of an effective coherence length 1 µm to 10 µm) of the curve 14A. The positions of the straight lines 14*a* and 14*b* can be freely adjusted in a case where the coherence length of the light source can be made variable. Analysis of a subject structure can be efficiently performed by analyzing detected signals P1/P0 corresponding to the coherence length of the light source. Furthermore, signals of higher S/N can be obtained by adding various kinds of arithmetic processing such as multiplying the detected signals P1/P0 by other detected signals (e.g., detected signals P0, detection signals (P0+P1), or the like) or comparing the detected signals P1/P0 with other detected signals, like a structural difference can be made clear in FIG. 10F by multiplying the optical path length standard deviation distribution that is an amount related to the detected signals P1/P0 by the light intensity distribution. The arithmetic processing for improving S/N may be performed in accordance with a change of a light emission intensity of the light source or a diaphragm of a lens (i.e., the amount of light that enters the light detection device 13). Alternatively, the arithmetic processing may be performed in accordance with a change of a direction of emission from the light source since the formula 15 is related to the movement speed v of a scatterer.

The coherence length of approximately 6 mm is short as laser, but is within a range of practical use in a multi-spectrum light source for reduced coherence such as a high-frequency superimposing semiconductor laser or a self-pulsation semiconductor laser. A semiconductor laser driven by a high-frequency superimposing circuit (in general, a frequency of 300 MHz) oscillates in a coherence length ranging from 0.1 mm to 0.2 mm, and can make the coherence length variable within a range from 0.2 mm to several tens of mm by changing the frequency, amplitude, or the like of the superimposing circuit (e.g., reducing the frequency). Furthermore, in a sweep light source (a light source that periodically sweeps a laser wavelength in a range of several tens of nm), a coherence length can be made variable within a range from 0.3 mm to several tens of mm by changing a wavelength fluctuation width or a cycle frequency. However, in a case where the sweep light source is used, the bandpass filter 9*p* is used in some cases to limit a wavelength of light that enters the light coupling layer 12. Furthermore, a desired coherence length can be obtained by combining a light source having a wide line width such as an LED and a bandpass filter having a narrow bandwidth. In this case, the bandpass filter may be disposed between the light source and a subject or between the subject and a light coupling layer. Furthermore, two or more light sources having different wavelengths may be used. When light from these light sources is scattered in the subject and enters the opening 9*a*, a beat occurs according to the principle described in FIG. 15C, and a coherence length becomes short. This is substantially the same as using a light source having a short coherence length. Also in this case, the bandpass filter 9*p* is used in some cases to limit a wavelength of light that enters the light coupling layer 12. Note that in a case where light sources having different wavelengths are used, the way in which a beat is generated changes and a distribution of effective coherence lengths also change when a light emission intensity ratio of the light sources is changed. Therefore, S/N may be improved by adding arithmetic processing according to the change of the light emission intensity ratio of the light sources to detected signals P1/P0.

Furthermore, a pulse light source may be used. In this case, a coherence length is equal to a pulse length (a value obtained by multiplying a pulse time width by light speed). In a case where the pulse light source is used, the relationships of a time coherence deterioration illustrated in FIGS. 9A through 9C are established. Meanwhile, in a case where the pulse light source is used, overlapping of wave trains is less likely (the probability that a certain wave train and a standard wave train are within the same wave train is low). This weakens the effect that the effective coherence length becomes short described in FIG. 8B. In this case, a pulse time width is selected so that the positions of the straight lines 14*a* and 14*b* (the effective coherence lengths of detected light) in FIG. 4A are within the fluctuating portion (the range from 1 µm to 10 µm) of the curve 14A.

As described above, use of the light detection device according to the present embodiment makes it possible to detect, as a difference between outputs of electrical signals, a difference between the gray matter 4*d* and the white matter 4*e* that are behind the skull 4*b* in the subject illustrated in FIGS. 10A through 10H. This makes it possible to markedly improve S/N as compared with a method (the second conventional example) of detecting a light intensity distribution image illustrated in FIG. 10B.

Second Embodiment

The present embodiment is different from First Embodiment in a configuration for guiding guided light 6*b* generated in a second transparent layer 12*b* to a detector 10A, and all of the other configurations are identical to those in First Embodiment. Elements that are identical to those in First Embodiment are given identical reference signs, and detailed description thereof is omitted.

Figure 11A:
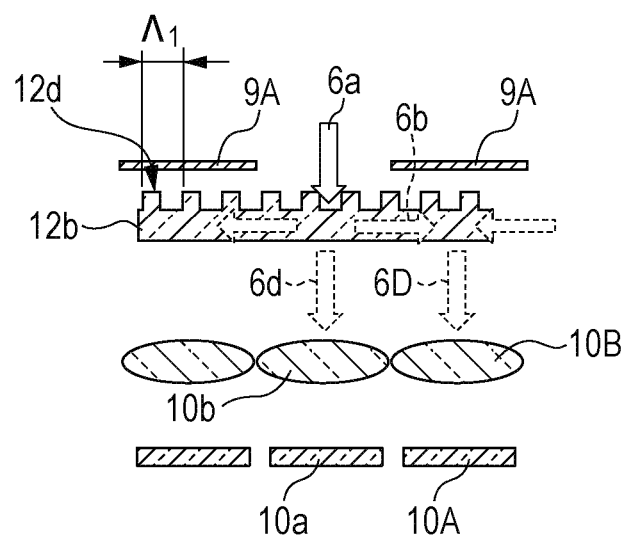
FIG. 11A is a cross-sectional view schematically illustrating a light detection device according to Second Embodiment.
Figure 11B:
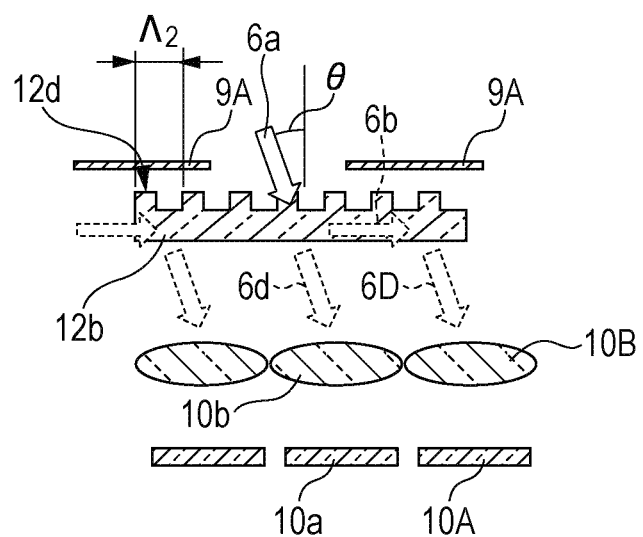
FIG. 11B is a cross-sectional view schematically illustrating the light detection device according to Second Embodiment.

FIGS. 11A and 11B illustrate a cross-sectional structure of a grating 12*d* and a waveguide layer (second transparent layer) 12*b* for guiding the guided light 6*b* to the detector 10A. FIG. 11A is a cross-sectional view including pixels in the vicinity of a central axis (on-axis position) of a light collecting lens 7 in FIG. 1A, and FIG. 11B is a cross-sectional view including pixels that are off the axis of the light collecting lens 7. In this form, in the off-axis position, the center of a light transmitting region 9*a* (a light shielding region 9A) and the center of a detector 10*a* (10A) are deviated from each other. Note that in the present disclosure, the expression "a detector is disposed so as to face a light shielding region or a light transmitting region" encompasses a form in which center positions thereof are deviated from each other as in the present embodiment. A pitch condition of the grating 12*d* in FIG. 11A is different from that in FIG. 11B. Specifically, the pitch in FIG. 11A is one (=Λ1)

obtained in a case where θ=0 in the formula 2, whereas the pitch in FIG. 11B is one (=Λ2) obtained in a case where θ≠0 in the formula 2. Accordingly, in FIG. 11A, the guided light 6b is generated both leftward and rightward on the paper on which FIG. 11A is drawn, whereas in FIG. 11B, the guided light 6b is generated either leftward or rightward (rightward in FIG. 11B) on the paper on which FIG. 11B is drawn. The guided light 6b thus generated is radiated directly below the light shielding region 9A so as to turn into radiated light 6D that enters the detector 10A. A value of θ in the formula 2 is determined in accordance with an incident angle of light from the light collecting lens 7. Although an image-side telecentric lens need be used as the light collecting lens 7 in First Embodiment, it is unnecessary to use an image-side telecentric lens as the light collecting lens 7 in Second Embodiment.

Figure 11C:
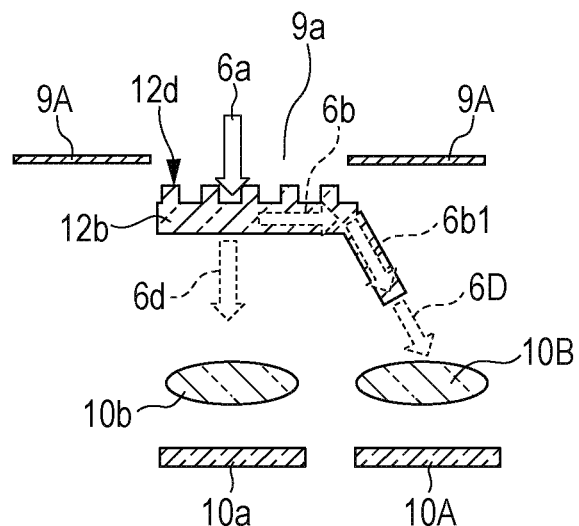
FIG. 11C is a cross-sectional view schematically illustrating another embodiment.

FIG. 11C is a diagram illustrating another form for guiding the guided light 6b to the detector 10A. Although the grating 12d is provided all over the entire surface in First Embodiment, the grating 12d is provided only directly below the light transmitting region 9a in FIG. 11C. The waveguide layer (second transparent layer) 12b is gradually bent toward the detector 10A side directly below the light shielding region 9A. Accordingly, the guided light 6b is also bent (guided light 6b1) along the waveguide layer (second transparent layer) 12b, radiated from an end surface of the waveguide layer (second transparent layer) 12b, and enters the detector 10A as radiated light 6D. Detection with a smaller light loss can be expected as compared with First Embodiment although a production process is complicated due to the bending of the waveguide layer (second transparent layer) 12b.

Figure 11D:
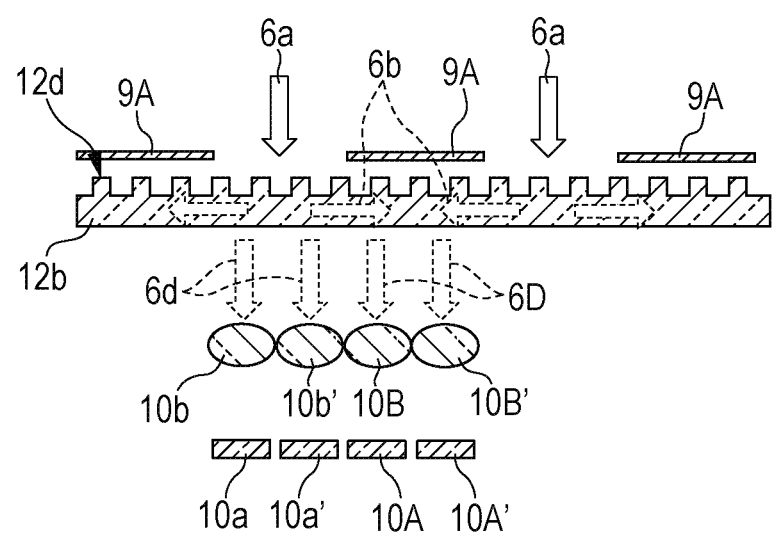
FIG. 11D is a cross-sectional view schematically illustrating another embodiment.
Figure 11E:
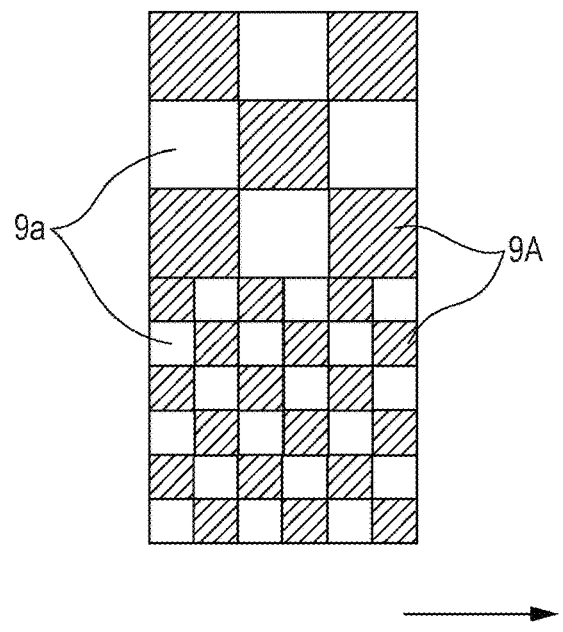
FIG. 11E is a plan view schematically illustrating another embodiment.
Figure 11F:
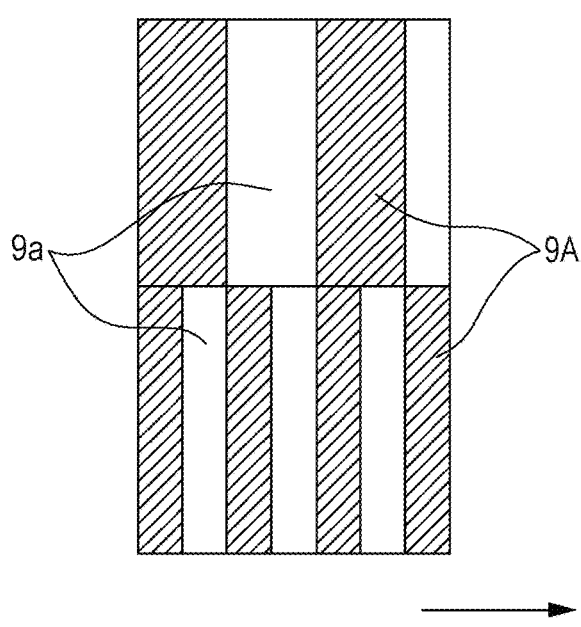
FIG. 11F is a plan view schematically illustrating another embodiment.

FIG. 11D is a diagram illustrating a form in which patterning of a reflection film that is the light shielding region 9A is different. In First Embodiment, a single microlens 10b (or 10B) and a single detector 10a (or 10A) correspond to the light transmitting region 9a (or the light shielding region 9A). Meanwhile, in the present embodiment, two microlenses 10b and 10b' (or 10B and 10B') and two detectors 10a and 10a' (or 10A and 10A') correspond to the light transmitting region 9a (or the light shielding region 9A). The two detectors 10a and 10a' (or 10A and 10A') are electrically conductive with each other. In this form, the length (light coupling length) of a grating coupler in a direction in which the guided light 6b travels is long. From the principle described in FIGS. 6A through 6J, in a case where the grating coupler is long, a difference is likely to occur in probability of occurrence of double pumping of incident light having a long coherence length. That is, there is an advantage of an increase of a range in which the light amount ratio P1/P0 illustrated in FIG. 4A changes. The curve 14C (condition C) of FIG. 4A indicates a result of calculation on the assumption that the width of the light transmitting region 9a and the light shielding region 9A in the xy plane is 5.6 μm×2 μm and a light source oscillates on the pulse condition (condition A) illustrated in FIG. 4B in the form of FIG. 11D. Since the light coupling length (the width of the light transmitting region 9a) is larger, the curve 14C is shifted toward a longer coherence length side from the curve 14A. Note that three or more microlenses 10b (or 10B) and three or more detectors 10a (or 10A) may correspond to the light transmitting region 9a (or the light shielding region 9A). As patterning of reflection films (the light shielding regions 9A), patterns of different pitches may be combined. For example, in FIG. 11E, the light transmitting regions 9a (or the light shielding regions 9A) form two checkered patterns of different pitches, and in FIG. 11F, the light transmitting regions 9a (or the light shielding regions 9A) form two striped patterns of different pitches. In both cases, the number of microlenses and detectors that correspond to a single light transmitting region 9a (or light shielding region 9A) is larger in a pattern of a wider pitch than in a pattern of a narrower pitch. For example, in the pattern of a narrower pitch, a single microlens and a single detector correspond to a single light transmitting region 9a (or light shielding region 9A) in the x-axis direction. In the pattern of a wider pitch, two microlenses and two detectors correspond to a single light transmitting region 9a (or light shielding region 9A) in the x-axis direction. Note that a direction of a grating vector of the grating is parallel with the x-axis direction, but may be changed depending on location.

Third Embodiment

The present embodiment is the same as First and Second Embodiments except for a signal arithmetic method in an arithmetic circuit 11, and elements that are identical to those in First and Second Embodiments are given identical reference signs, and detailed description thereof is omitted.

Figure 12:
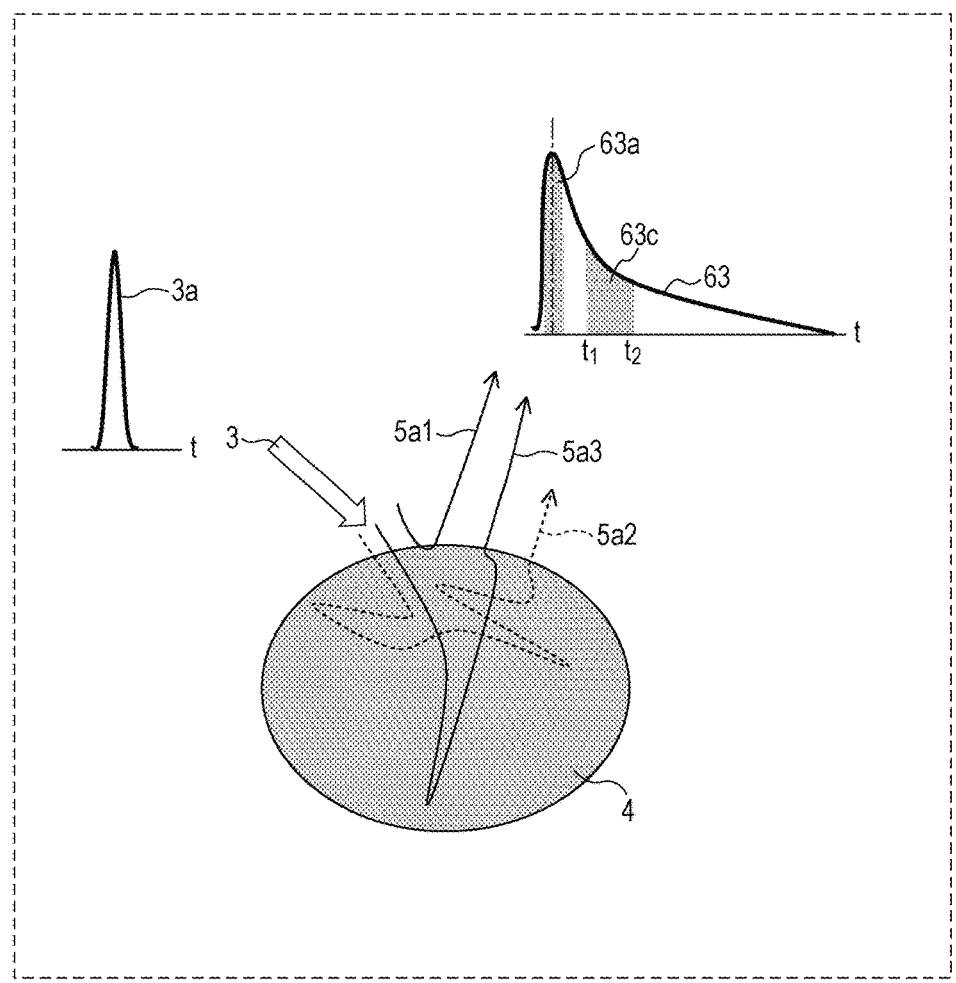
FIG. 12 is a cross-sectional explanatory view schematically illustrating a light detection method according to Third Embodiment.

FIG. 12 is an explanatory view illustrating a relationship between oscillation of a light source 2 and a detected signal in the present embodiment. The light source 2 oscillates a pulse 3a under control of a control circuit 1, light 3 scatters in a subject 4 and is received by detectors 10a and 10A via a light transmitting region 9a, and a signal 63 is detected. In FIG. 12, the vertical axis represents a detection intensity, and the horizontal axis represents an elapsed time. The signal 63 corresponds to a light amount P0 (or P0+P1) where P0 is the amount of light detected by the detector 10a and P1 is the amount of light detected by the detector 10A. A time width of the signal 63 is wider than that of the original pulse 3a due to the influence of a variation in optical path length caused by scattering. An output 63a at the beginning of the signal 63 is a signal of light 5a1 reflected by a surface of the subject 4. An output 63c between a time t1 and a time t2 of the signal 63 is a signal of light 5a2 and 5a3 scattered in the subject 4. Although the optical path length of the light 5a2 and the optical path length of the light 5a3 are equal to each other, the light 5a2 draws a light path propagating in the vicinity of a superficial layer due to a large amount of backscattering, whereas the light 5a3 draws a light path reaching a deep layer due to a small amount of backscattering. As is clear from the description in FIGS. 9A through 9C, a coherence length is easy to deteriorate in a case where the amount of forward scattering is large, and a coherence length is hard to deteriorate in a case where the amount of backscattering is large. Accordingly, a ratio of forward scattering and backscattering is reflected in the light amount ratio P1/P0 of the light 5a2 and the light 5a3. In the present embodiment, the arithmetic circuit 11 detects the output 63c by time resolving of the signal 63 and generates an image. That is, light between the time t1 and the time t2 in which the light 5a2 and 5a3 scattered in the subject 4 is detected, and an image is generated as intensity distribution information in each detector. Furthermore, the arithmetic circuit 11 distinguishes an image based on the output 63c in accordance with the value of the light amount ratio P1/P0. Specifically, for example, a first image made up of pixels whose light amount ratios P1/P0 are equal to or larger than a threshold value is generated. That is, the first image is generated as information of a distribution of light amounts detected by detectors corresponding to the pixels whose light amount ratios P1/P0 are equal to or larger than the threshold value. Furthermore, a second image made up of pixels whose light amount ratios P1/P0 are smaller than the threshold value may be generated. That is, the second image may be generated as information of a distribution of light amounts detected by detectors corresponding to the pixels whose light amount ratios P1/P0 are smaller than the threshold value. Although the light 5$a$2 and the light 5$a$3 cannot be distinguished from each other in the second conventional example, the light 5$a$2 and the light 5$a$3 can be distinguished from each other in the present embodiment since a ratio of forward scattering and back-scattering is reflected in the light amount ratio P1/P0. This makes it possible to analyze an inside of the subject 4 in accordance with the depth. Note that various arithmetic processing such as multiplying detected signals P1/P0 by other detection signals (e.g., detected signals P0, detected signals (P0+P1), or the like) or comparing the detected signals P1/P0 with other detected signals as in First Embodiment. Furthermore, arithmetic processing of the detected signals P1/P0 or other detected signals may be added to the output 63$c$.

What is claimed is:

1. A light detection system comprising:
    a light detection device; and
    a light source,
    the light detection device including:
    a light detector that has a main surface and includes at least one first detector and at least one second detector that are disposed along the main surface;
    a light coupling layer disposed on or apart from the light detector, the light coupling layer including:
        a first low-refractive-index layer,
        a first high-refractive-index layer that is disposed on the first low-refractive-index layer and includes a first grating, and
        a second low-refractive-index layer that is disposed on the first high-refractive-index layer,
        the first high-refractive-index layer having a higher refractive index than the first low-refractive-index layer and the second low-refractive-index layer; and
    a light shielding film disposed on the light coupling layer, the light shielding film including:
        at least one light transmitting region and at least one light shielding region adjacent to the at least one light transmitting region,
    wherein the first high-refractive-index layer is disposed between the light detector and the light shielding film.

2. The light detection system according to claim 1, further comprising an arithmetic circuit that, in operation, calculates a ratio of a first signal detected by the at least one first detector and a second signal detected by the at least one second detector.

3. The light detection system according to claim 2, wherein
    the at least one first detector comprises first detectors;
    the at least one second detector comprises second detectors;
    the first detectors and the second detectors are two-dimensionally disposed along the main surface;
    the at least one light transmitting region comprises light transmitting regions;
    the at least one light shielding region comprises light shielding regions;
    each of the light transmitting regions corresponds to at least one of the first detectors;
    each of the light shielding regions corresponds to at least one of the second detectors; and
    the arithmetic circuit, in operation, calculates the ratio for each of the first detectors and generates an image indicative of a distribution of the ratios in the light detector.

4. The light detection system according to claim 3, further comprising a control circuit that, in operation, changes a coherence length of light emitted from the light source, and
    the arithmetic circuit, in operation, generating, for each coherence length changed by the control circuit, the image indicating the distribution of the ratios.

5. The light detection system according to claim 3, wherein
    the arithmetic circuit, in operation, calculates, for each of the first detectors, the ratio by using the first signal detected by each of the first detectors within a predetermined time range and the second signal detected by each of the second detectors within the predetermined time range; and
    the arithmetic circuit, in operation, generates a first image indicative of a distribution of the first signal detected, within the predetermined time range, by a first detector for which the ratio is equal to or larger than a threshold value among the first detectors and a second image indicative of a distribution of the first signal detected, within the predetermined time range, by a first detector for which the ratio is smaller than the threshold value among the first detectors.

6. The light detection system according to claim 1, further comprising an arithmetic circuit that, in operation, calculates at least one selected from the group consisting of proportion of a first signal detected by the at least one first detector and proportion of a second signal detected by the at least one second detector in a sum of the first signal and the second signal.

7. The light detection system according to claim 6, wherein
    the at least one first detector comprises first detectors;
    the at least one second detector comprises second detectors;
    the first detectors and the second detectors are two-dimensionally disposed along the main surface;
    the at least one light transmitting region comprises light transmitting regions;
    the at least one light shielding region comprises light shielding regions;
    each of the light transmitting regions corresponds to at least one of the first detectors;
    each of the light shielding regions corresponds to at least one of the second detectors; and
    the arithmetic circuit, in operation, calculates, for each of the first detectors, at least one selected from the group consisting of the proportion of the first signal and the proportion of the second signal in the sum and generates an image indicative of a distribution of the at least one selected from the group consisting of the proportion of the first signal and the proportion of the second signal in the sum in the light detector.

8. The light detection system according to claim 7, further comprising a control circuit that, in operation, changes a coherence length of light emitted from the light source, and
    the arithmetic circuit, in operation, generating, for each coherence length changed by the control circuit, the image indicative of the distribution of the at least one selected from the group consisting of the proportion of the first signal and the proportion of the second signal in the sum.

9. The light detection system according to claim 7, wherein
the arithmetic circuit, in operation, calculates, for each of the first detectors, at least one selected from the group consisting of the proportion of the first signal and the proportion of the second signal in the sum by using the first signal detected by each of the first detectors within a predetermined time range and the second signal detected by each of the second detectors within the predetermined time range; and
the arithmetic circuit, in operation, generates a first image indicative of a distribution of the first signal detected, within the predetermined time range, by a first detector for which the proportion of the first signal in the sum is equal to or larger than a threshold value or the proportion of the second signal in the sum is equal to or smaller than the threshold value among the first detectors and a second image indicative of a distribution of the first signal detected, within the predetermined time range, by a first detector for which the proportion of the first signal in the sum is smaller than the threshold value or the proportion of the second signal in the sum is larger than the threshold value among the first detectors.

10. The light detection system according to claim 1, wherein
the light source, in operation, emits pulsed light.

11. The light detection system according to claim 1, wherein
the light detection device further includes a bandpass filter that is disposed on the light coupling layer and, in operation, selectively transmits a wavelength of light emitted by the light source.

12. The light detection system according to claim 1, further comprising a control circuit that, in operation, changes a coherence length of light emitted from the light source.

13. The light detection system according to claim 1, wherein
a light that enters the light coupling layer through the at least one light transmitting region is divided into a first part and a second part,
the first part of the light is extracted from a first region of the light coupling layer which overlaps the at least one light transmitting region in a thickness direction of the light coupling layer,
the second part of the light is extracted from a second region of the light coupling layer which overlaps the at least one light shielding region in the thickness direction of the light coupling layer,
the first part of the light is directed to the at least one first detector, and
the second part of the light is directed to the at least one second detector.

14. A light detection device comprising:
a light detector that has a main surface and includes at least one first detector and at least one second detector that are disposed along the main surface;
a light coupling layer disposed on or apart from the light detector, the light coupling layer including:
a first low-refractive-index layer,
a first high-refractive-index layer that is disposed on the first low-refractive-index layer and includes a first grating, and
a second low-refractive-index layer that is disposed on the first high-refractive-index layer,
the first high-refractive-index layer having a higher refractive index than the first low-refractive-index layer and the second low-refractive-index layer; and
a light shielding film disposed on the light coupling layer, the light shielding film including:
at least one light transmitting region and at least one light shielding region adjacent to the at least one light transmitting region,
wherein the first high-refractive-index layer is disposed between the light detector and the light shielding film.

15. The light detection device according to claim 14, wherein
the at least one first detector comprises first detectors;
the at least one second detector comprises second detectors;
the first detectors and the second detectors are two-dimensionally disposed along the main surface;
the at least one light transmitting region comprises light transmitting regions;
the at least one light shielding region comprises light shielding regions;
each of the light transmitting regions corresponds to at least one of the first detectors; and
each of the light shielding regions corresponds to at least one of the second detectors.

16. The light detection device according to claim 15, wherein
the light shielding regions are disposed in a striped pattern or a checkered pattern in plan view.

17. The light detection device according to claim 14, wherein
the light detector further includes:
a first microlens disposed between the at least one first detector and the light coupling layer; and
a second microlens disposed between the at least one second detector and the light coupling layer.

18. The light detection device according to claim 14, wherein
the light coupling layer further includes:
a third low-refractive-index layer; and
a second high-refractive-index layer that is disposed between the third low-refractive-index layer and the first low-refractive-index layer and includes a second grating; and
the second high-refractive-index layer has a higher refractive index than the first low-refractive-index layer and the third low-refractive-index layer.

19. The light detection device according to claim 14, wherein
a light that enters the light coupling layer through the at least one light transmitting region is divided into a first part and a second part,
the first part of the light is extracted from a first region of the light coupling layer which overlaps the at least one light transmitting region in a thickness direction of the light coupling layer,
the second part of the light is extracted from a second region of the light coupling layer which overlaps the at least one light shielding region in the thickness direction of the light coupling layer,
the first part of the light is directed to the at least one first detector, and
the second part of the light is directed to the at least one second detector.

20. An optical device comprising:
a light coupling layer including:
- a first low-refractive-index layer,
- a first high-refractive-index layer that is disposed on the first low-refractive-index layer and includes a first grating, and
- a second low-refractive-index layer that is disposed on the first high-refractive-index layer,
- the first high-refractive-index layer having a higher refractive index than the first low-refractive-index layer and the second low-refractive-index layer; and a light shielding film disposed on the light coupling layer, the light shielding film including:
- at least one light transmitting region and at least one light shielding region adjacent to the at least one light transmitting region, wherein the at least one light transmitting region includes two light transmitting regions disposed adjacent to one of the at least one light shielding region, and the first grating overlaps both of the two light transmitting regions in a thickness direction of the light coupling layer.

21. The optical device according to claim 20, wherein the first high-refractive-index layer is disposed between the first low-refractive-index layer and the second low-refractive-index layer, and the first grating overlaps the at least one light shielding region in the thickness direction of the light coupling layer.

22. A light detection device comprising:
a light detector that has a main surface and includes at least one first detector and at least one second detector that are disposed along the main surface;

a light coupling layer disposed on or apart from the light detector, the light coupling layer including:
- a first low-refractive-index layer,
- a first high-refractive-index layer that is disposed on the first low-refractive-index layer and includes a first grating, and
- a second low-refractive-index layer that is disposed on the first high-refractive-index layer,
- the first high-refractive-index layer having a higher refractive index than the first low-refractive-index layer and the second low-refractive-index layer; and a light shielding film disposed on the light coupling layer, the light shielding film including:
- at least one light transmitting region and at least one light shielding region adjacent to the at least one light transmitting region, the at least one light transmitting region overlaps at least a portion of the at least one first detector in a thickness direction of the light detection device, and the at least one light shielding region overlaps at least a portion of the at least one second detector in the thickness direction.

23. A light detection system comprising:
a light detection device; and
a light source,
the light detection device including:
a light detector that has a main surface and includes at least one first detector and at least one second detector that are disposed along the main surface;

a light coupling layer disposed on or apart from the light detector, the light coupling layer including:
- a first low-refractive-index layer,
- a first high-refractive-index layer that is disposed on the first low-refractive-index layer and includes a first grating, and
- a second low-refractive-index layer that is disposed on the first high-refractive-index layer,
- the first high-refractive-index layer having a higher refractive index than the first low-refractive-index layer and the second low-refractive-index layer; and a light shielding film disposed on the light coupling layer, the light shielding film including:
- at least one light transmitting region and at least one light shielding region adjacent to the at least one light transmitting region, the at least one light transmitting region overlaps at least a portion of the at least one first detector in a thickness direction of the light detection device, and the at least one light shielding region overlaps at least a portion of the at least one second detector in the thickness direction.

* * * * *